United States Patent
Kokubo et al.

(10) Patent No.: US 12,186,060 B2
(45) Date of Patent: Jan. 7, 2025

(54) BLOOD PRESSURE-RELATED INFORMATION DISPLAY DEVICE, BLOOD PRESSURE-RELATED INFORMATION DISPLAY METHOD, AND COMPUTER-READABLE RECORDING MEDIUM

(71) Applicants: OMRON HEALTHCARE CO., LTD., Muko (JP); JICHI MEDICAL UNIVERSITY, Tokyo (JP)

(72) Inventors: Ayako Kokubo, Kyoto (JP); Mitsuo Kuwabara, Kyoto (JP); Shingo Yamashita, Kyoto (JP); Kazuomi Kario, Tochigi (JP)

(73) Assignees: OMRON HEALTHCARE CO., LTD., Muko (JP); JICHI MEDICAL UNIVERSITY, Tokyo (JP)

( * ) Notice: Subject to any disclaimer, the term of this patent is extended or adjusted under 35 U.S.C. 154(b) by 633 days.

(21) Appl. No.: 17/484,422

(22) Filed: Sep. 24, 2021

(65) Prior Publication Data
US 2022/0007951 A1    Jan. 13, 2022

Related U.S. Application Data

(63) Continuation of application No. PCT/JP2020/008976, filed on Mar. 3, 2020.

(30) Foreign Application Priority Data

Mar. 25, 2019    (JP) ................................. 2019-057000

(51) Int. Cl.
*A61B 5/021*    (2006.01)
*A61B 5/00*    (2006.01)

(52) U.S. Cl.
CPC ...... *A61B 5/02125* (2013.01); *A61B 5/02108* (2013.01); *A61B 5/02116* (2013.01);
(Continued)

(58) Field of Classification Search
None
See application file for complete search history.

(56) References Cited

U.S. PATENT DOCUMENTS 5,178,154 A * 1/1993 Ackmann ............ A61B 5/0535
600/526
2006/0116731 A1 * 6/2006 Kramer .................... A61B 8/08
607/17

(Continued)

FOREIGN PATENT DOCUMENTS

CN    104398257 A    3/2015
JP    2003-290174 A    10/2003
(Continued)

OTHER PUBLICATIONS

S. Manikandan. "Measures of dispersion." J Pharmacol Pharmacother. Oct.-Dec. 2011; 2(4): 315-316. (Year: 2011).*

(Continued)

*Primary Examiner* — Meredith Weare
(74) *Attorney, Agent, or Firm* — Oliff PLC

(57) ABSTRACT

According to the present invention, blood pressure surges are detected from time-series data on blood pressure of a subject that varies with pulsation based on predetermined determination criteria. For each blood pressure surge thus detected, an envelope connecting a plurality of pulse-corresponding peaks forming the blood pressure surge is acquired as an individual waveform. Statistical processing is performed on a plurality of individual waveforms to obtain a representative waveform and waveform variation among the blood pressure surges in the time-series data. On a display (Continued)

MT3

| PULSE NUMBER | 1 | 2 | 3 | 4 | 5 | 6 | 7 | 8 | 9 | PEAK POSITION (10) | 11 | 12 | 13 | 14 | 15 | 16 | 17 |
|---|---|---|---|---|---|---|---|---|---|---|---|---|---|---|---|---|---|
| SURGE NO.1 | 0 | 0 | 0 | 0 | 4 | 10 | 13 | 17 | 24 | 29 | 25 | 20 | 15 | 11 | 3 | 0 | 0 |
| SURGE NO.2 | 0 | 2 | 3 | 5 | 8 | 12 | 15 | 19 | 20 | 21 | 18 | 14 | 10 | 7 | 4 | 4 | 2 |
| MEAN WAVEFORM | 0 | 1 | 1.5 | 2.5 | 6 | 11 | 14 | 18 | 22 | 25 | 21.5 | 17 | 12.5 | 9 | 3.5 | 2 | 1 | screen, a curve indicating the representative waveform is displayed with the curve superimposed on a region indicating the waveform variation among the blood pressure surges.

9 Claims, 15 Drawing Sheets

(52) U.S. Cl.
CPC .......... *A61B 5/7264* (2013.01); *A61B 5/7282* (2013.01); *A61B 5/742* (2013.01)

(56) References Cited

U.S. PATENT DOCUMENTS

| | | | | |
|---|---|---|---|---|
| 2006/0200011 | A1* | 9/2006 | Suzuki | A61B 5/02125 |
| | | | | 600/301 |
| 2013/0296717 | A1* | 11/2013 | Takenoshita | A61B 5/7221 |
| | | | | 600/479 |
| 2017/0209055 | A1* | 7/2017 | Pantelopoulos | A61B 5/02438 |
| 2018/0256050 | A1* | 9/2018 | Kuwabara | G16H 15/00 |
| 2019/0388037 | A1* | 12/2019 | Kokubo | A61B 5/6824 |

FOREIGN PATENT DOCUMENTS

| | | |
|---|---|---|
| JP | 2014-168574 A | 9/2014 |
| JP | 2018-153232 A | 10/2018 |
| WO | 2017/082107 A1 | 5/2017 |

OTHER PUBLICATIONS

English machine translation of JP-2003290174-A. Retrieved Jun. 1, 2024. (Year: 2024).*
English machine translation of CN-104398257-A. Retrieved Jun. 1, 2024. (Year: 2024).*
English machine translation of JP-2018153232-A. Retrieved Jun. 1, 2024. (Year: 2024).*
Jun. 2, 2020 Search Report issued in International Patent Application No. PCT/JP2020/008976.
Dec. 29, 2023 Office Action issued in Chinese Patent Application No. 202080024289.4.
Aug. 28, 2024 Office Action issued in Chinese Patent Application No. 202080024289.4.

* cited by examiner

Fig.11

| SURGE NO. | START TIME | PEAK TIME | END TIME | ... |
|---|---|---|---|---|
| 1 | 22:20:15 | 22:20:21 | 22:20:26 | |
| 2 | 22:25:35 | 22:25:44 | 22:25:52 | |
| ... | | | | |

| RECORDED TIME | SBP | DBP | PR | ... |
|---|---|---|---|---|
| 22:20:14 | 129 | 82 | 60 | |
| 22:20:15 | 130 | 78 | 61 | |
| 22:20:16 | 134 | 80 | 60 | |
| 22:20:17 | 140 | 90 | 60 | |
| 22:20:18 | 143 | 91 | 61 | |
| 22:20:19 | 147 | 97 | 59 | |
| 22:20:20 | 154 | 103 | 60 | |
| 22:20:21 | 159 | 108 | 60 | |
| 22:20:22 | 155 | 108 | 60 | |
| 22:20:23 | 150 | 99 | 61 | |
| 22:20:24 | 145 | 94 | 60 | |
| 22:20:25 | 141 | 90 | 60 | |
| 22:20:26 | 133 | 82 | 61 | |
| 22:20:27 | 132 | 80 | 60 | |

MT2

TIME-SERIES DATA ON SURGE NO.1

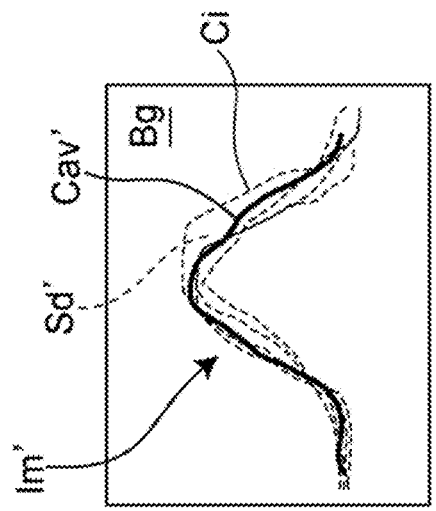
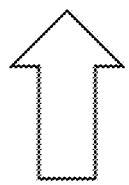
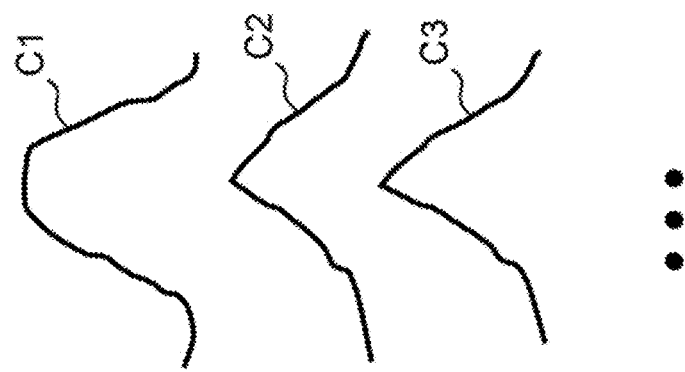
Fig.16B
Fig.16A

BLOOD PRESSURE-RELATED INFORMATION DISPLAY DEVICE, BLOOD PRESSURE-RELATED INFORMATION DISPLAY METHOD, AND COMPUTER-READABLE RECORDING MEDIUM

CROSS-REFERENCE TO RELATED APPLICATION

This application is based on an application No. 2019-057000 filed in Japan on Mar. 25, 2019, the entire content of which is hereby incorporated by reference.

TECHNICAL FIELD

The present invention relates to a blood pressure-related information display device and a blood pressure-related information display method, and more particularly to a device and a method for displaying information on a blood pressure surge of a subject in a visualized form. The present invention further relates to a computer-readable recording medium storing a program for causing a computer to execute the blood pressure-related information display method.

BACKGROUND ART

It is known that, when a patient suffering from sleep apnea syndrome (SAS) resumes breathing after apnea, the blood pressure sharply rises and then falls. Herein, such a rapid blood pressure variation is referred to as a "blood pressure surge" (or simply a "surge"). Displaying information on the blood pressure surge occurring in the patient in a visualized form is considered to be useful for diagnosis and treatment of SAS.

In the related art, for example, in FIG. 3 of Patent Literature 1 (WO 2017/082107 A1), a waveform of variation (a blood pressure surge) for a patient suffering from sleep apnea syndrome (SAS) is displayed in graph form.

SUMMARY OF INVENTION

However, as disclosed in Patent Literature 1, a waveform of blood pressure surges is merely displayed with a time axis for time-series data on a systolic blood pressure (SBP) value enlarged to make a peak for each pulse clearly visible, and is not displayed as a curve (shape) indicating a rising or falling trend in blood pressure.

Under such circumstances, the present applicants have filed a patent application for an invention for classifying patterns (shapes) of waveforms of blood pressure surges of patients suffering from SAS and displaying them in a visualized form (Japanese Patent Application No. 2017-050066). This allows a doctor to grasp the patterns of a waveform of blood pressure surges of each patient suffering from SAS within a relatively short time. It would be further convenient for the doctor to view, in a superimposed manner, a representative waveform and waveform variation among blood pressure surges of each patient suffering from SAS. Further, viewing the representative waveform and waveform variation among blood pressure surges of not only patients suffering from SAS but also subjects is considered to be useful as information for use in evaluation of a cardiovascular disease risk or information for use in evaluation of a disease risk of a specific organ.

It is therefore an object of the present invention to provide a blood pressure-related information display device and a blood pressure-related information display method that allow a representative waveform and waveform variation among blood pressure surges to be displayed in a superimposed manner. It is another object of the present invention to provide a computer-readable recording medium storing a program for causing a computer to execute the blood pressure-related information display method.

In order to achieve the above object, a blood pressure-related information display device according to the present disclosure is a blood pressure-related information display device that displays information on a blood pressure surge in a visualized form, the blood pressure surge corresponding to a phenomenon in which blood pressure rises over a plurality of pulses to reach a peak and then falls over a plurality of pulses, the blood pressure-related information display device comprising:

a blood pressure surge detection part configured to detect, based on predetermined determination criteria, blood pressure surges from time-series data on blood pressure of a subject that varies with pulsation;

an individual waveform acquisition part configured to acquire, for each blood pressure surge detected, an envelope connecting a plurality of pulse-corresponding peaks forming the blood pressure surge as an individual waveform;

a statistical processing part configured to perform statistical processing on a plurality of individual waveforms acquired to obtain a representative waveform and waveform variation among the blood pressure surges in the time-series data; and a display processing part configured to display, on a display screen, a curve indicating the representative waveform with the curve superimposed on a region indicating the waveform variation among the blood pressure surges, wherein the statistical processing part creates, in a memory area, an equivalent state where the plurality of individual waveforms are relatively slid in a horizontal direction to align positions of peaks of the plurality of individual waveforms on a coordinate plane including abscissae representing a lapse of time and ordinates representing blood pressure variation amounts due to the blood pressure surges, and performs the statistical processing on blood pressure variation amount data on the plurality of individual waveforms for each of the abscissae to obtain the representative waveform and the waveform variation, and the statistical processing part sets, for an individual waveform that is shorter in horizontal dimension than a longest individual waveform among the plurality of individual waveforms, a contribution of a pulse equivalent portion shorter than the longest individual waveform to zero for the statistical processing on the blood pressure variation amount data.

As used herein, the "predetermined determination criteria" typically refer to criteria for detection of a blood pressure surge of a patient suffering from sleep apnea syndrome (SAS). For example, as disclosed in Japanese Patent Application No. 2017-048946 and Japanese Patent Application No. 2017-050066, the "predetermined determination criteria" refer to that a range from a surge start point to a surge peak point falls within a peak detection section (for example, a period of 15 pulses), that a difference (a blood pressure variation amount) between a systolic blood pressure value at the surge start point and a systolic blood pressure value at the peak point is equal to or greater than 20 mmHg (or 15 mmHg), that a period between the surge start point and the peak point is longer than a period of five pulses, and that a period between the peak point and a surge end point is longer than a period of seven pulses.

Further, the plurality of "pulse-corresponding peaks" forming the blood pressure surge used to create the envelope refers to peaks corresponding to systolic blood pressure in a continuous instantaneous blood pressure waveform. Note that the "pulse-corresponding peaks" may refer to peaks corresponding to a diastolic blood pressure (DBP) value.

Further, the "statistical processing" refers to processing of averaging the individual waveforms or processing of obtaining a median of the individual waveforms. The "representative waveform" among the blood pressure surges refers to, for example, a mean waveform obtained as a result of averaging the plurality of individual waveforms, a waveform corresponding to a median of the plurality of individual waveforms, or the like. The "waveform variation" among the blood pressure surges refers to, for example, a width of distribution of the plurality of individual waveforms.

Further, the "display screen" typically refers to a screen of a display device, but may be, for example, a paper surface output by a printer.

Further, for example, the "display" of the curve indicating the representative waveform on the display screen is typically provided in a mode where abscissae represent the lapse of time (for example, progress of pulses) and ordinates represent blood pressure variation amounts due to the blood pressure surges.

Herein, a "peak of the individual waveform" refers to a peak of each blood pressure surge and corresponds to a maximum pulse-corresponding peak among a plurality of pulse-corresponding peaks forming the blood pressure surge.

Further, the "equivalent state" means that data in the memory area only needs to be in a state equivalent to a state defined on the coordinate plane without the necessity of actually drawing and aligning the positions of the peaks of the plurality of individual waveforms on the coordinate plane.

In another aspect, a blood pressure-related information display method according to the present disclosure is a blood pressure-related information display method for displaying information on a blood pressure surge in a visualized form, the blood pressure surge corresponding to a phenomenon in which blood pressure rises over a plurality of pulses to reach a peak and then falls over a plurality of pulses, the blood pressure-related information display method comprising steps of:

detecting, based on predetermined determination criteria, blood pressure surges from time-series data on blood pressure of a subject that varies with pulsation;

acquiring, for each blood pressure surge detected, an envelope connecting a plurality of pulse-corresponding peaks forming the blood pressure surge as an individual waveform; and performing statistical processing on a plurality of individual waveforms acquired to obtain a representative waveform and waveform variation among the blood pressure surges in the time-series data, wherein on a coordinate plane including abscissae representing a lapse of time and ordinates representing blood pressure variation amounts due to the blood pressure surges, an equivalent state where the plurality of individual waveforms are relatively slid in a horizontal direction to align positions of peaks of the plurality of individual waveforms is created in a memory area, and the statistical processing is performed on blood pressure variation amount data on the plurality of individual waveforms for each of the abscissae to obtain the representative waveform and the waveform variation, and for an individual waveform that is shorter in horizontal dimension than a longest individual waveform among the plurality of individual waveforms, a contribution of a pulse equivalent portion shorter than the longest individual waveform is set to zero for the statistical processing on the blood pressure variation amount data; and further comprising displaying, on a display screen, a curve indicating the representative waveform with the curve superimposed on a region indicating the waveform variation among the blood pressure surges.

In yet another aspect, a computer-readable recording medium according to the present disclosure is a computer-readable recording medium non-transitorily storing a program for causing a computer to execute the above blood pressure-related information display method.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIG. 11 is a diagram illustrating a table where times each identifying a detected blood pressure surge are recorded.

FIG. 12 is a diagram illustrating a table where time-series data on pulse-corresponding peaks of an individual waveform is recorded for a certain blood pressure surge.

FIG. 16A is a diagram illustrating a plurality of individual waveforms obtained for the apnea period, similar to FIG. 9A. FIG. 16B is a diagram illustrating a modification of the display of the waveform variation.

DESCRIPTION OF EMBODIMENT

An embodiment of the present invention will be described in detail below with reference to the drawings.
(Configuration of System)

Figure 1:
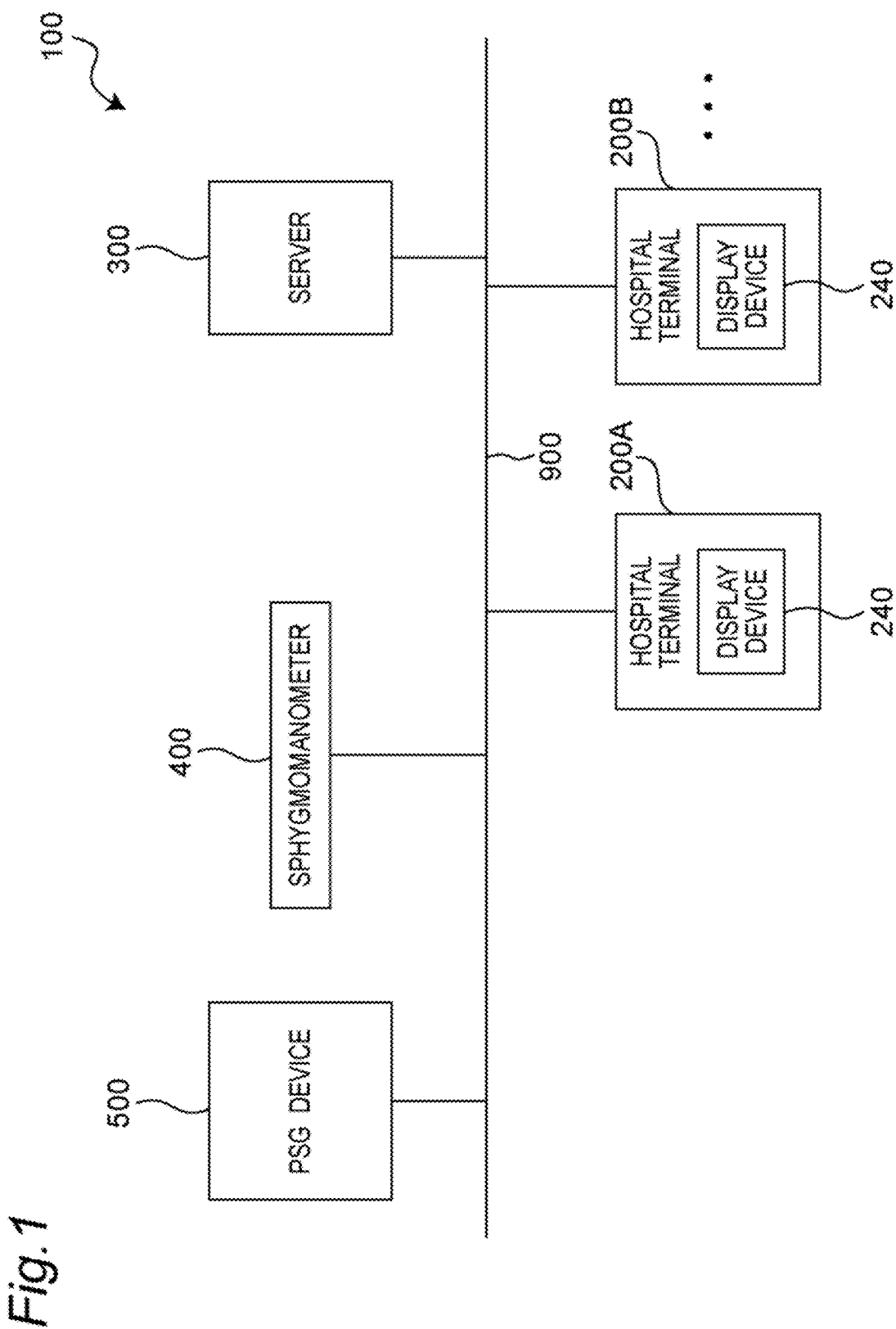
FIG. 1 is a block diagram illustrating an embodiment where a blood pressure-related information display device according to the present invention is configured as a system on a network.

FIG. 1 illustrates an example where a blood pressure-related information display device according to the present invention is configured as a system (denoted by a reference numeral 100) of an embodiment on a network. The system 100 includes hospital terminals 200A, 200B, each including a display device 240 as a display screen, a server 300, a tonometry sphygmomanometer 400, and a polysomnography (PSG) device 500. The hospital terminals 200A, 200B, the server 300, the sphygmomanometer 400, and the PSG device 500 can communicate with each other over a network 900, which is an in-hospital local area network (LAN). Communication over the network 900 may be established by radio or wire. According to the present embodiment, the network 900 is an in-hospital local area network (LAN), but is not limited to the in-hospital LAN. The network 900 may be another type of network such as the Internet or may be one-to-one communication using a USB cable or the like. Note that only two hospital terminals 200A, 200B are illustrated in this example, but three or more hospital terminals may be provided.

Figure 2:
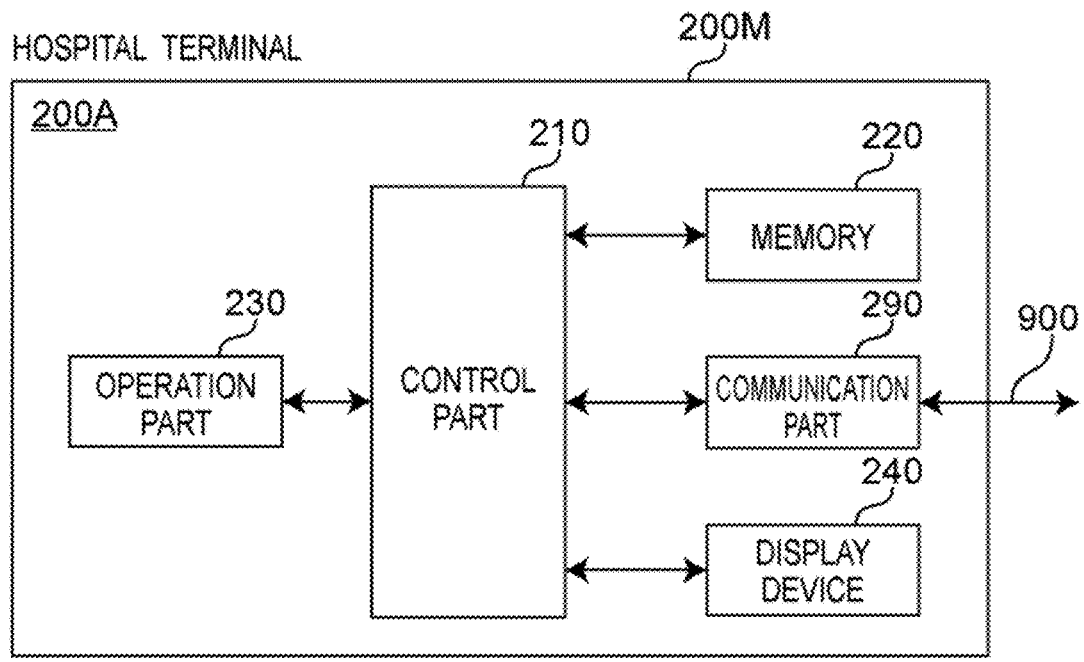
FIG. 2 is a block diagram illustrating a configuration of a hospital terminal included in the system.

As illustrated in FIG. 2, the hospital terminal 200A includes a main body 200M, and includes a control part 210, a memory 220, an operation part 230, the display device 240 as the display screen, and a communication part 290 contained on the main body 200M. The hospital terminal 200A is a commercially available laptop personal computer having application software (computer program) installed therein so as to perform processing to be described later, and the hospital terminal 200A has access to the server 300.

The control part 210 includes a central processing unit (CPU) and an auxiliary circuit of the CPU, controls each component of the hospital terminal 200A, and performs processing to be described later in accordance with a program and data stored in the memory 220. That is, data input from the operation part 230 and the communication part 290 is processed, and the data thus processed is stored in the memory 220, displayed on the display device 240, or output from the communication part 290.

The memory 220 includes a random access memory (RAM) used as a work area necessary for the control part 210 to execute a program, and a read only memory (ROM) for storing a basic program to be executed by the control part 210. Further, a semiconductor memory (memory card, solid state drive (SSD)) or the like may be used as a storage medium of a secondary storage device serving as an auxiliary for a storage area of the memory 220.

In this example, the operation part 230 includes a keyboard and a mouse, and typically inputs an operation signal indicating an operation by a doctor as a user to the control part 210. Further, the operation part 230 may include another operation device such as a touchscreen instead of or in addition to the keyboard and the mouse.

The display device 240 includes a display screen (for example, a liquid crystal display (LCD), an electroluminescence (EL) display, or the like). The display device 240 is controlled by the control part 210 to display a predetermined image on the display screen.

The communication part 290 transmits information from the control part 210 to the server 300 over the network 900.

Although not illustrated for the sake of simplicity, the other hospital terminals 200B, . . . are identical in configuration to the hospital terminal 200A.

Figure 3:
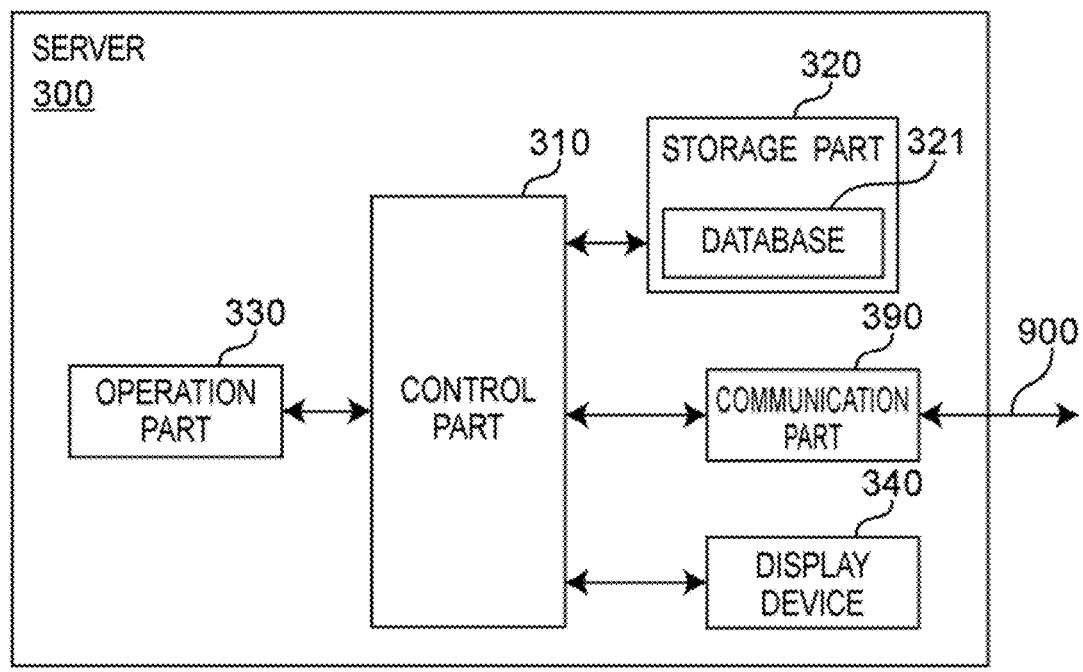
FIG. 3 is a block diagram illustrating a configuration of a server included in the system.

As illustrated in FIG. 3, the server 300 includes a control part 310, a storage part 320, an operation part 330, a display device 340, and a communication part 390. The server 300 is a general-purpose computer device having a program (software) installed therein so as to perform processing to be described later.

The control part 310 includes a CPU and an auxiliary circuit of the CPU, controls each component of the server 300, performs predetermined processing in accordance with a program and data stored in the storage part 320, processes data input from the operation part 330 and the communication part 390, and stores the data thus processed in the storage part 320, displays the processed data on the display device 340, or outputs the processed data from the communication part 390.

The storage part 320 includes a RAM used as a work area necessary for the control part 310 to execute a program, and a ROM for storing a basic program to be executed by the control part 310. The storage part 320 is provided with a database 321 containing blood pressure measurement data transmitted from many subjects. Further, a magnetic disk (hard disk (HD), flexible disk (FD)), an optical disc (compact disc (CD), digital versatile disc (DVD), Blu-ray disc (BD)), a magneto-optical disk (MO), a semiconductor memory (memory card, SSD), or the like may be used as a storage medium of a secondary storage device serving as an auxiliary for a storage area of the storage part 320.

In this example, the operation part 330 includes a keyboard and a mouse, and inputs an operation signal indicating an operation by the user to the control part 310. Further, the operation part 330 may include another operation device such as a touchscreen instead of or in addition to the keyboard and the mouse.

The display device 340 includes a display screen (for example, an LCD, an EL display, or the like). The display device 340 is controlled by the control part 310 to display a predetermined image on the display screen.

The communication part 390 transmits information from the control part 310 to another device (the hospital terminal 200A in this example) over the network 900, receives information transmitted from another device over the network 900, and passes the information to the control part 310.

Figure 4:
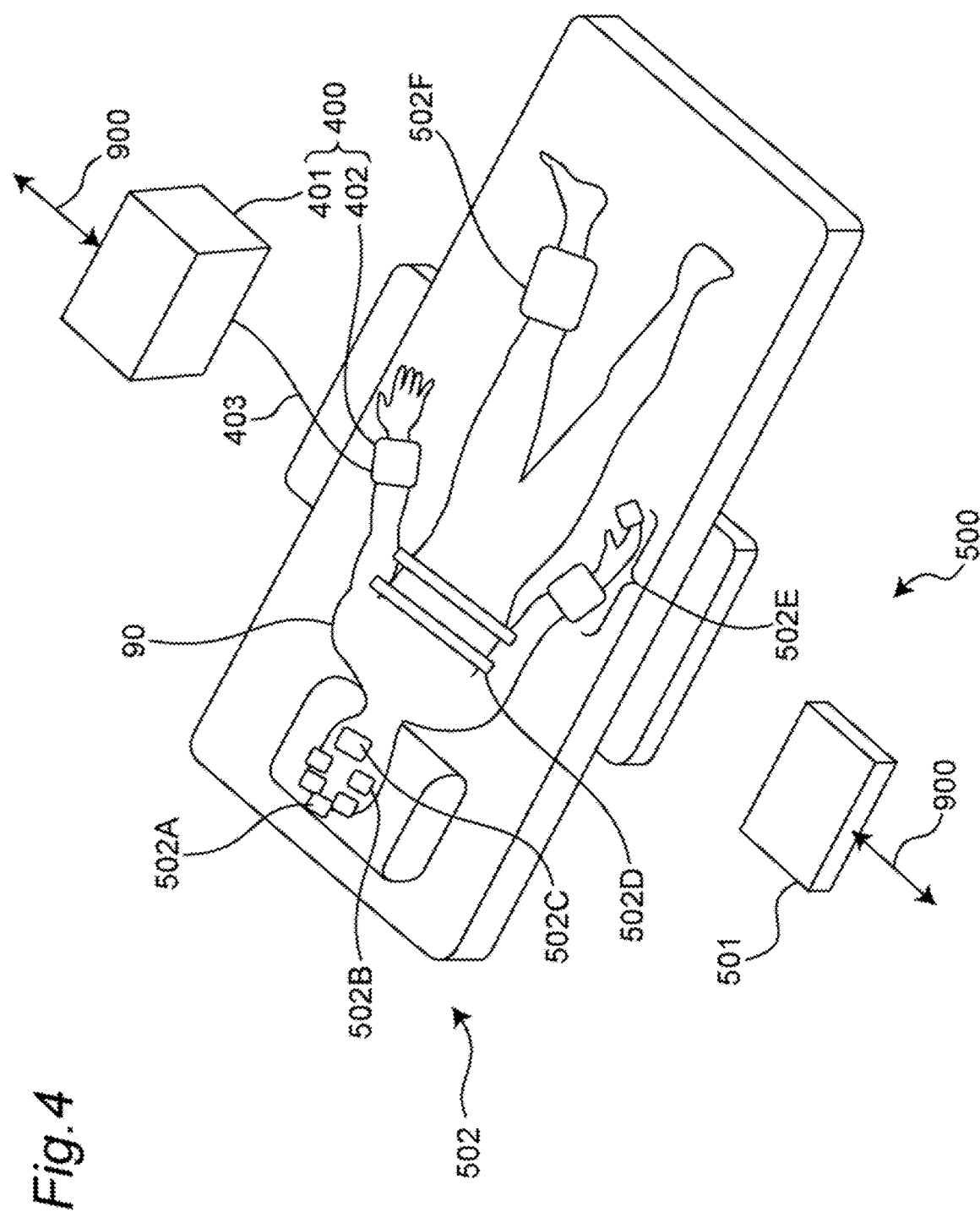
FIG. 4 is a diagram illustrating a state where time-series data on blood pressure of a subject for one night and a physical condition that may become a factor in blood pressure surge are measured together by the system.
Figure 6A:
FIG. 6A is a diagram illustrating time-series data on blood pressure of a subject for one night.

In this example, the sphygmomanometer 400 illustrated in FIG. 1 is a tonometry sphygmomanometer as disclosed in Japanese Patent Application No. 2017-050066. As illustrated in FIG. 4, the sphygmomanometer 400 includes a pressure sensor part 402 that continuously detects a pressure pulse wave of a radial artery passing through a to-be-measured part (for example, the left wrist) of a subject 90 for each pulse by tonometry, and a main unit 401 that outputs changes in pressure detected by the pressure sensor part 402 as blood pressure time-series data. The pressure sensor part 402 and the main unit 401 are connected by a signal cable 403. Tonometry is a method under which, with a blood vessel pressed to be flat by the pressure sensor part 402 (for example, a pressure pulse wave sensor), blood pressure is determined based on a result of measurement of the pressure pulse wave. When the blood vessel is regarded as a circular tube having a uniform thickness, a relational expression between an internal pressure (blood pressure) of the blood vessel and an external pressure (pressure exerted by the pressure pulse wave) of the blood vessel can be derived in accordance with Laplace's law with consideration given to a wall of the blood vessel, regardless of the flow of blood in the blood vessel and the presence or absence of pulsation. Under the condition where the blood vessel is pressed to be flat on a pressed surface, this relational expression can make the pressure exerted by the pressure pulse wave and the blood pressure equal to each other by approximating the radii of the outer wall and inner wall of the blood vessel. Therefore, hereinafter, the pressure exerted by the pressure pulse wave is equal to the blood pressure. As a result, the sphygmomanometer 400 measures the blood pressure value of the to-be-measured part (for example, the left wrist) for each pulse, and outputs blood pressure time-series data 801 in which a measurement time (time) is associated with blood pressure as illustrated in FIG. 6A, for example. The blood pressure time-series data 801 for one night contains pulse-corresponding peaks (peaks corresponding to systolic blood pressure (SBP) or diastolic blood pressure (DBP)) for about 30,000 pulses.

Further, the PSG device 500 illustrated in FIG. 1 is a commercially available PSG device (for example, Neurofax (registered trademark) EEG-9200 manufactured by NIHON KOHDEN CORPORATION) in this example, and is used only when [B. applied blood pressure-related information display method] to be described later is executed. As illustrated in FIG. 4, the PSG device 500 includes a sensor group 502 and a main unit 501 that processes signals from the sensor group 502 and outputs information specifying a physical condition of the subject 90. In this example, the sensor group 502 includes a brain wave detection electrode 502A that detects brain waves, an eye movement detection electrode 502B that detects eye movement, an air flow sensor 502C that detects air flow caused by respiration, an electrocardiogram electrode 502D that obtains an electrocardiogram, a pulse oximeter 502E that detects percutaneous arterial oxygen saturation ($SpO_2$), and an electromyogram electrode 502F that obtains an electromyogram. The sensor group 502 and the main unit 501 are connected by a signal cable (not illustrated) via a cable box (not illustrated). In this example, the PSG device 500 can output information indicating an apnea period (or hypopnea period), a REM sleep period, a non-REM sleep period, an awakening period, and/or a period in which $SpO_2$ is low as information indicating a period in which the physical condition of the subject 90 is specified (this is referred to as a "physical condition specifying period"). "Apnea" during sleep refers to a "cessation of breathing for 10 seconds or more". Further, "hypopnea" refers to a state where a rate of ventilation by respiration is equal to or less than 50% for 10 seconds or more. Further, "REM sleep" refers to sleep with rapid eye movement, "non-REM sleep" refers to sleep without rapid eye movement, and "awakening" refers to a state of waking up. $SpO_2$ refers to a value obtained as a result of measuring, through the skin (percutaneously), how much oxygen binds to hemoglobin contained in red blood cells flowing in arterial blood. The period in which $SpO_2$ is "low" refers to a period in which $SpO_2$ is less than 90% in this example.

Figure 6B:
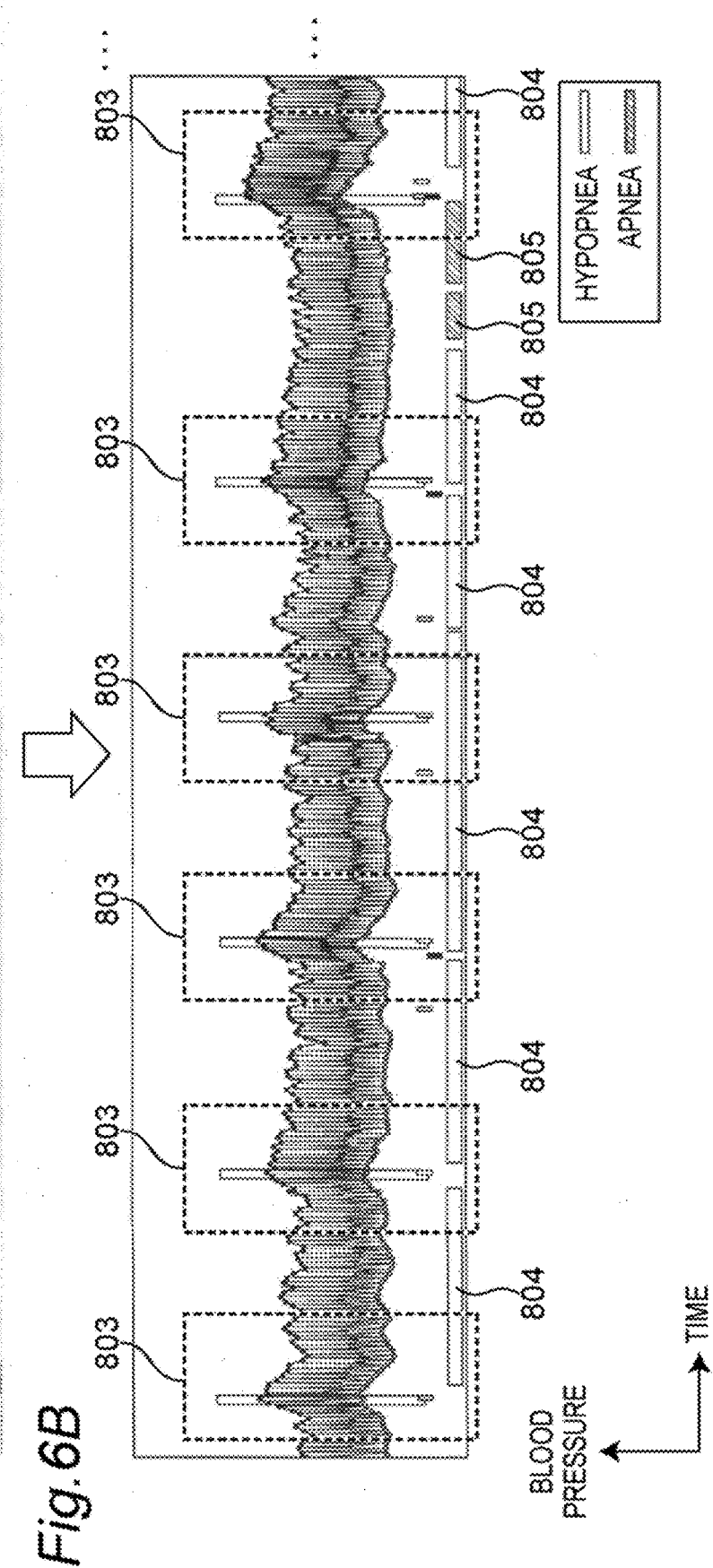
FIG. 6B is an enlarged view of a part of FIG. 6A, illustrating blood pressure surges detected on the time-series data and apnea/hypopnea events measured by a PSG device.

For example, in FIG. 6B that is an enlarged view of a part of FIG. 6A, the "apnea" period is indicated by hatched bars 805, 805, . . . . Further, the "hypopnea" period is indicated by white bars 804, 804, . . . . As described above, the PSG device 500 can output a plurality of types of information indicating the physical condition specifying period for the subject 90.

(Blood Pressure-Related Information Display Method)

The system 100 can execute, when roughly divided, the following [A. basic blood pressure-related information display method] and [B. applied blood pressure-related information display method], each including creation of image data in the server 300 and display of the image data in the hospital terminal (for example, 200A).

[A. Basic Blood Pressure-Related Information Display Method]

Under the basic blood pressure-related information display method, image data is created and displayed as follows using only the blood pressure time-series data 801 in which the measurement time (time) and the blood pressure output from the sphygmomanometer 400 are associated with each other as illustrated in FIG. 6A without using the PSG device 500.

Figure 5A:
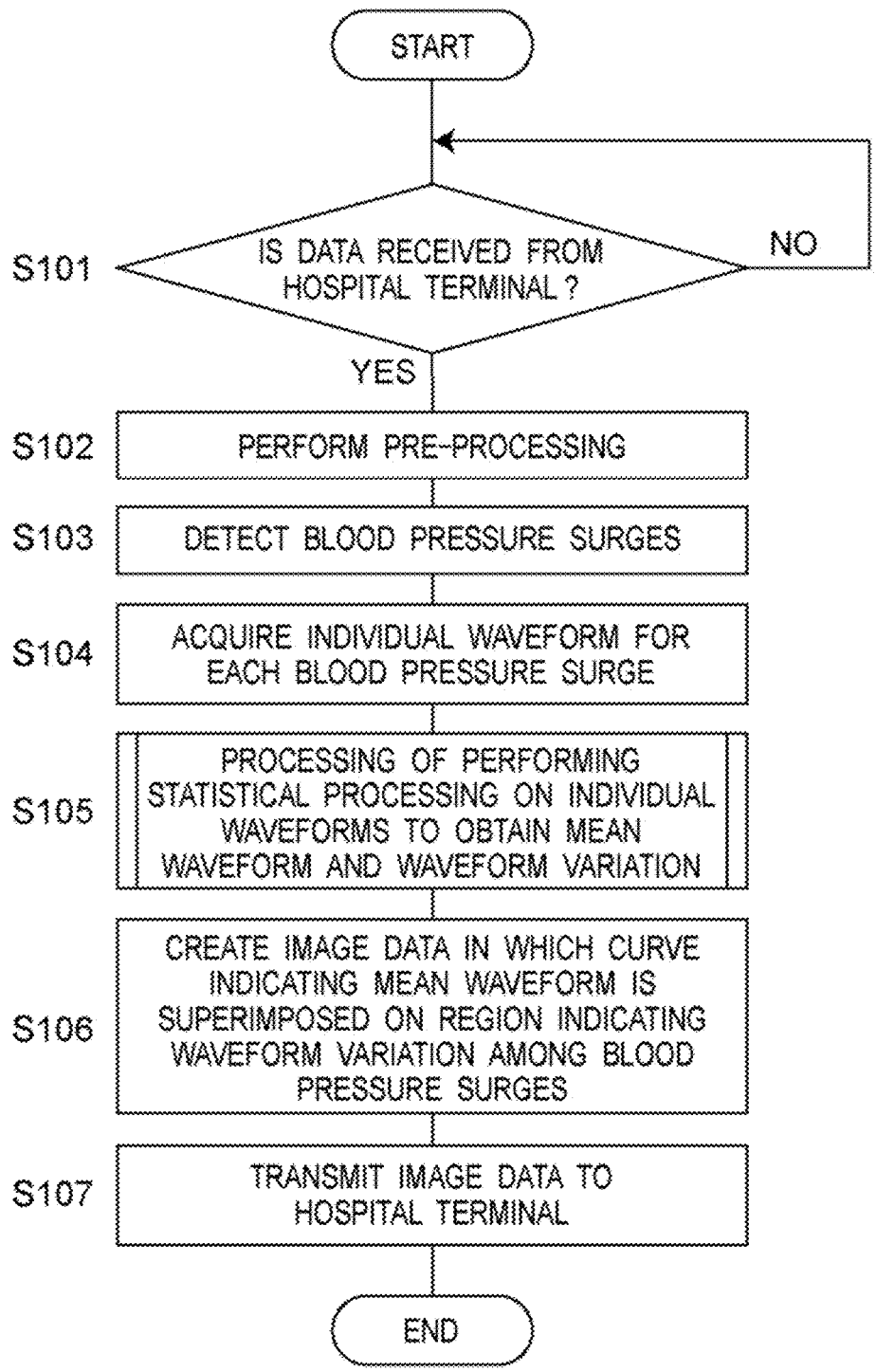
FIG. 5A is a diagram illustrating an operation flow of the server when executing a basic blood pressure-related information display method.

(Creation of Image Data in Server 300)

i) In a state illustrated in FIG. 4, it is assumed that continuous blood pressure measurement using the sphygmomanometer 400 is performed on the subject 90 all night (including the sleep period) (in this example, it is assumed that the physical condition is not measured using the PSG device 500). In this example, the blood pressure time-series data from the sphygmomanometer 400 is received by the hospital terminal 200A and temporarily stored in the memory 220. Subsequently, for example, a doctor as a user operates the operation part 230 of the hospital terminal 200A to transmit the blood pressure time-series data measured for the subject 90 together with the information indicating the physical condition specifying period to the server 300 over the network 900.

ii) In this example, the server 300 is in a continuous operation state (but a maintenance period or the like is excluded) and waits for data from the hospital terminal 200A as shown in step S101 in FIG. 5A (illustrating an operation flow of the server 300 when executing the basic blood pressure-related information display method). Upon receipt of the above-described blood pressure time-series data from the hospital terminal 200A via the communication part 390 serving as an input part from the network 900 (YES in step S101), the control part 310 of the server 300 stores the blood pressure time-series data thus received into the database 321 of the storage part 320. Then, the following steps S102 to S107 are executed.

iii) First, as shown in step S102, the control part 310 acts as a pre-processing part to perform pre-processing such as smoothing the blood pressure time-series data and removing noise from the blood pressure time-series data using a well-known moving average or the like, or removing high frequency components from the blood pressure time-series data using a low-pass filter.

iv) Next, as shown in step S103, the control part 310 acts as a blood pressure surge detection part to detect a blood pressure surge from the blood pressure time-series data on the subject 90 based on predetermined determination criteria as disclosed in, for example, Japanese patent application No. 2017-048946 and Japanese Patent Application No. 2017-050066. As a result, for example, a plurality of blood pressure surges are detected as indicated by dashed-line rectangular frames 803, 803, . . . in FIG. 6B. It is said that several hundred blood pressure surges may occur for one night. In this example, peaks corresponding to systolic blood pressure (SBP) are denoted by black dots (●) and are connected by an envelope. Further, peaks corresponding to diastolic blood pressure (DBP) are denoted by white dots (○) and are connected by an envelope.

Figure 7:
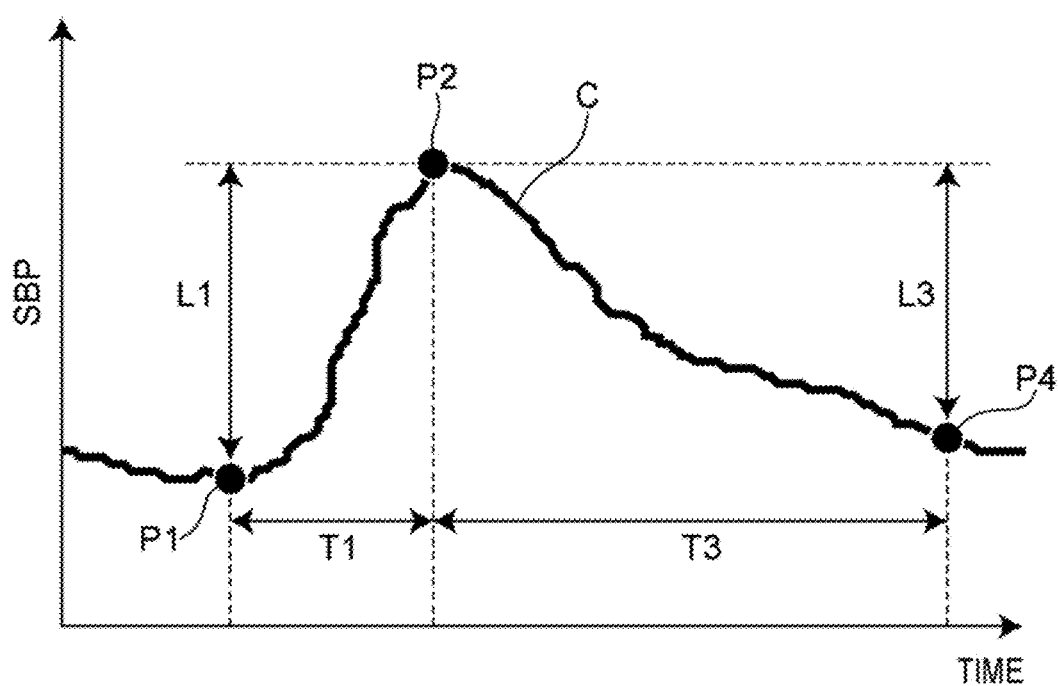
FIG. 7 is a diagram for describing determination criteria for detection of each blood pressure surge with an example of a waveform (individual waveform) of a blood pressure surge.

The "predetermined determination criteria" for detection of a blood pressure surge refer to, as illustrated in FIG. 7 (in which an example of the individual waveform of the blood pressure surge is represented by a curve C), for example, that a range from a surge start point P1 to a surge peak point P2 falls within a peak detection section (for example, a period of 15 pulses), that a difference (blood pressure variation amount) L1 between a systolic blood pressure (SBP) value at the surge start point P1 and a systolic blood pressure (SBP) value at the peak point P2 is equal to or greater than 20 mmHg (or 15 mmHg), that a period T1 between the surge start point P1 and the peak point P2 is longer than a period of five pulses, and that a period T3 between the peak point P2 and a surge end point P4 is longer than a period of seven pulses. In this example, the surge start point P1 is defined as a point before the peak point P2 where the systolic blood pressure value (SBP) becomes the lowest. The surge end point P4 is defined as a point after the peak point P2 where the blood pressure falls by L1×0.75 (=L3) from the peak point P2.

v) Next, as shown in step S104 in FIG. 5A, the control part 310 acts as an individual waveform acquisition part to acquire, for each of the detected blood pressure surges 803, 803, . . . , an envelope connecting a plurality of pulse-corresponding peaks (in this example, peaks corresponding to systolic blood pressure (SBP)) forming the blood pressure surge 803 as an individual waveform. As illustrated in FIG. 7, the individual waveform of the blood pressure surge is represented as a curve C having a mountain shape.

vi) Next, as shown in step S105 in FIG. 5A, the control part 310 acts as a statistical processing part to perform statistical processing on all the individual waveforms thus acquired to obtain a representative waveform and waveform variation among the blood pressure surges in the time-series data 801 in this example. The "statistical processing" refers to processing of averaging the individual waveforms. In this example, the "representative waveform" among the blood pressure surges refers to a mean waveform obtained as a result of averaging the plurality of individual waveforms. Further, in this example, the "waveform variation" among the blood pressure surges refers to a width of distribution of the plurality of individual waveforms.

Figure 8:
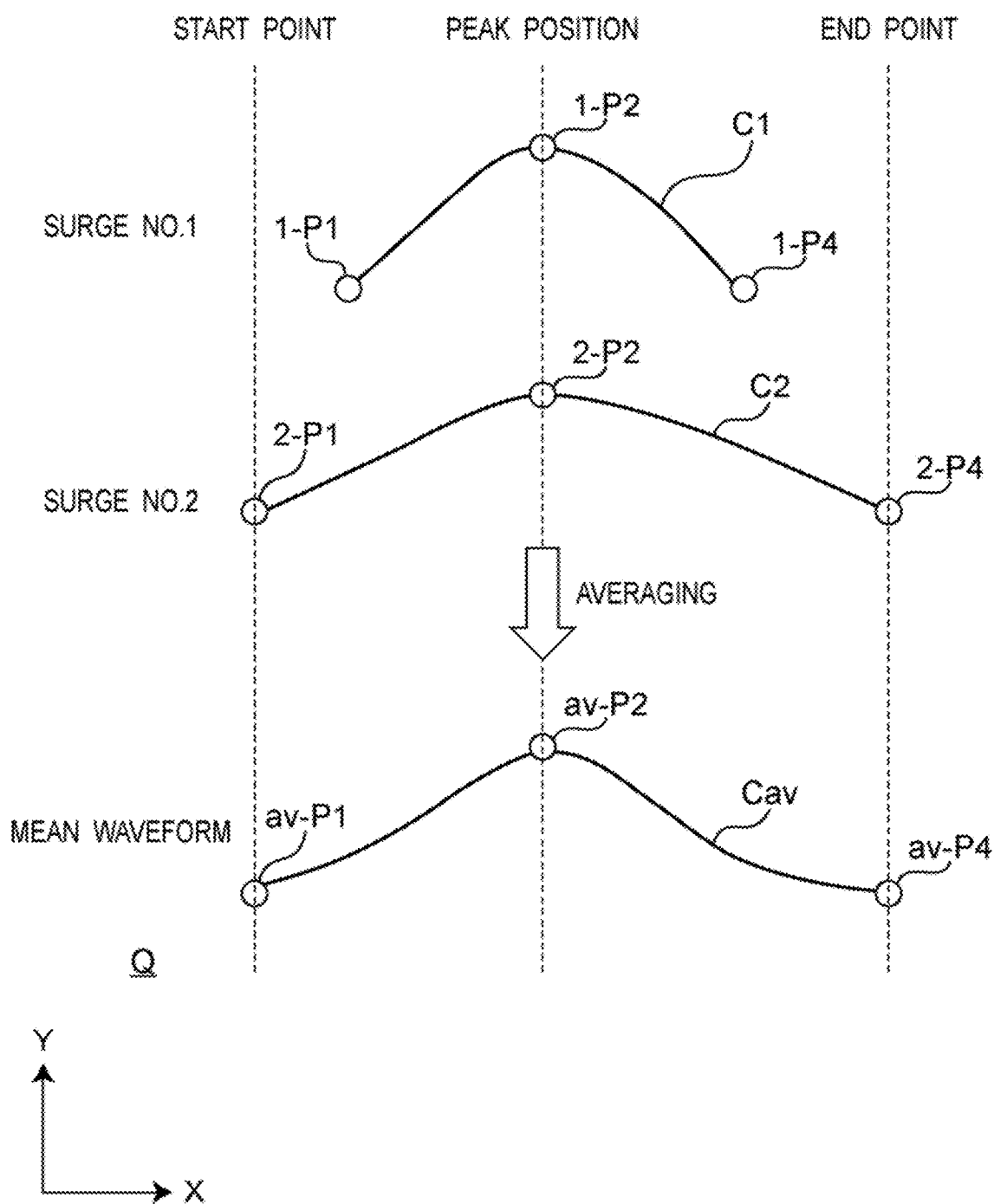
FIG. 8 is a diagram for conceptually describing processing of averaging individual waveforms of blood pressure surges.

Conceptually, the processing of averaging the individual waveforms of the blood pressure surges is as follows. As illustrated in FIG. 8, it is assumed that an individual waveform C1 denoted by "surge No. 1" and an individual waveform C2 denoted by "surge No. 2" exist as blood pressure surges. In this case, the processing of averaging the individual waveforms of the blood pressure surges corresponds to processing of obtaining a curve Cav indicating the mean waveform as the representative waveform by averaging blood pressure variation amount data on the plurality of individual waveforms C1, C2 for each abscissae X with the plurality of individual waveforms C1, C2 relatively slid in a horizontal direction X on a coordinate plane Q including the abscissae X representing the lapse of time and the ordinates Y representing the blood pressure variation amounts due to the blood pressure surges to align the positions of the peaks of the plurality of individual waveforms C1, C2. In FIG. 8, the abscissae X indicating the lapse of time are identified by pulse numbers specifying the pulse-corresponding peaks. The ordinates Y are identified by the blood pressure variation amounts in systolic blood pressure (SBP) value due to the blood pressure surges. Note that specific data processing (statistical processing on the individual waveforms of the blood pressure surges) will be described later in detail.

In this example, a range of the "waveform variation" among the blood pressure surges is defined as a range of ±k times (where, k is a natural number) the standard deviation σ for each abscissa X using the standard deviation σ of the distribution (distribution for each abscissa X) of the blood pressure variation amount data on the plurality of individual waveforms. Typically, k is set to 1, 2 or 3. Hereinafter, unless otherwise specified, it is assumed that the range of the "waveform variation" among the blood pressure surges is a range of ±σ. The display of a region (for example, a region Sd illustrated in FIG. 9B to be described later) indicating the waveform variation ±σ is particularly useful when the waveform variation among the individual waveforms is enough to be treated as a normal distribution (for example, several tens or more).

As a result, the curve Cav indicating the mean waveform as the representative waveform and the waveform variation ±σ for each abscissa X are obtained.

vii) Next, as shown in step S106 in FIG. 5A, the control part 310 acts as a part of a display processing part to create image data in which the curve Cav indicating the mean waveform is superimposed on the region (denoted by Sd) indicating the waveform variation among the blood pressure surges.

Figure 9A:
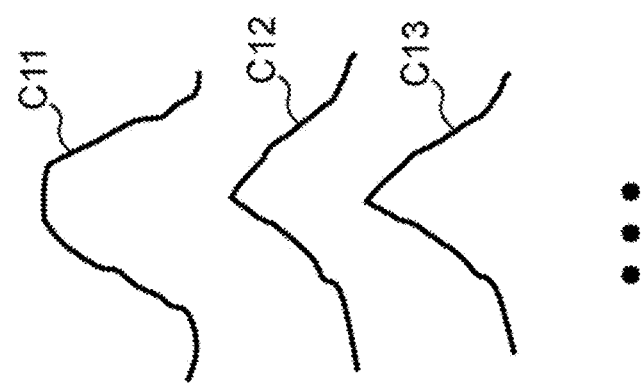
FIG. 9A is a diagram illustrating a plurality of individual waveforms.
Figure 9B:
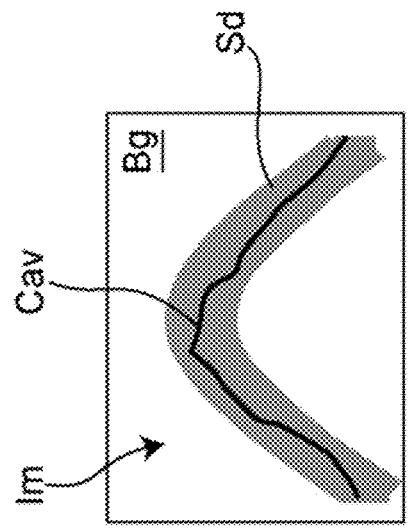
FIG. 9B is a diagram illustrating image data where a curve indicating a mean waveform is superimposed on a region indicating a waveform variation.

For example, as illustrated in FIG. 9A, it is assumed that individual waveforms C11, C12, C13, . . . are obtained in step S104 in FIG. 5A. In this case, by step S106 in FIG. 5A, for example, as illustrated in FIG. 9B, image data Im in which the curve Cav indicating the mean waveform is superimposed on the region Sd indicating the waveform variation is obtained. In this example, the curve Cav indicating the mean waveform is represented by a solid line having a certain density. The region Sd indicating the waveform variation is represented as a region having an intermediate density between the density of the curve Cav and the density of a background region (in this example, a white region) Bg.

viii) Subsequently, as shown in step S107 in FIG. 5A, the control part 310 of the server 300 transmits, over the network 900, the image data Im thus created to the hospital terminal 200A, which is a provider of the blood pressure time-series data in this example.

Note that the control part 310 of the server 300 may transmit the image data Im to the hospital terminal 200B or the like other than the hospital terminal 200A, for example, in accordance with an instruction issued by the user who operates the hospital terminal 200A.

(Statistical Processing on Individual Waveforms of Blood Pressure Surges)

Figure 10:
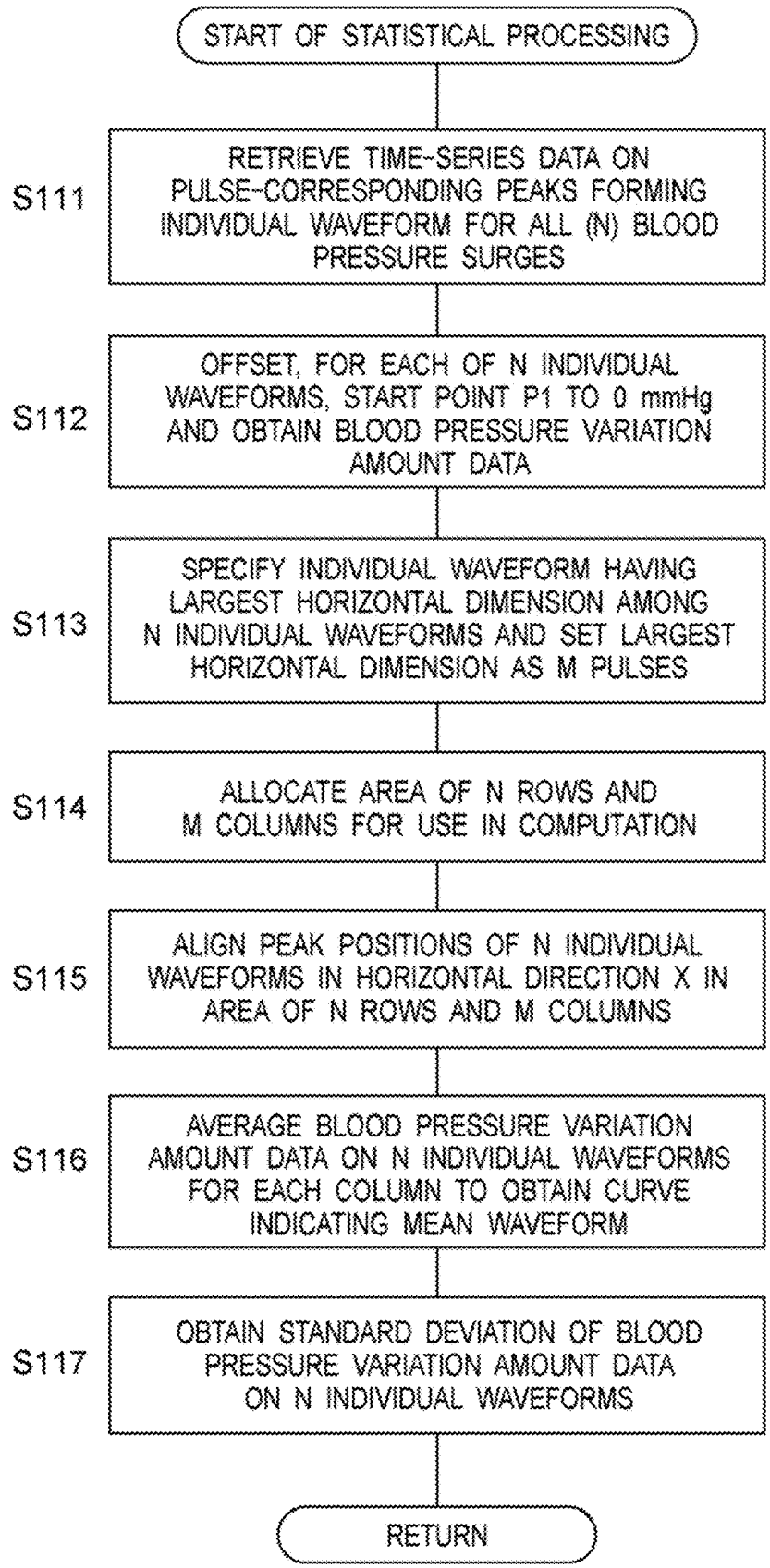
FIG. 10 is a diagram illustrating a detailed flow of statistical processing on individual waveforms of blood pressure surges.

FIG. 10 illustrates a detailed flow of the statistical processing on the individual waveforms of the blood pressure surges performed by the control part 310 of the server 300, as shown in step S105 in FIG. 5A.

As shown in step S111 in FIG. 10, the control part 310 retrieves, from the database 321, time-series data on the pulse-corresponding peaks forming the individual waveform for all the detected blood pressure surges. In this example, it is assumed that N blood pressure surges are obtained.

For example, as shown in a table MT1 in FIG. 11, the detected blood pressure surge No. 1 is identified by a start time (time of start point) 22:20:15, a peak time (time of peak) 22:20:21, and an end time (time of end point) 22:20:26. Further, the blood pressure surge No. 2 is identified by a start time 22:25:35, a peak time 22:25:44, and an end time 22:25:52. Note that the time notation is "hour:minute:second" (the same applies hereinafter).

In this case, for example, for the blood pressure surge No. 1, as shown in a table MT2 in FIG. 12, the time-series data on the pulse-corresponding peaks of the individual waveform is recorded such that, at the start time 22:20:15, a peak corresponding to SBP as the pulse-corresponding peak is 130 [mmHg], a peak corresponding to DBP is 78 [mmHg], and a pulse rate PR is 61 [pulses/minute]. At 22:20:16 corresponding to the next pulse, the peak corresponding to SBP is recorded as 134 [mmHg], the peak corresponding to DBP is recorded as 80 [mmHg], and the pulse rate PR is recorded as 60 [pulses/minute]. As described above, the time-series data on the pulse-corresponding peaks is sequentially recorded, and at the end time 22:20:26, the peak corresponding to SBP is recorded as 133 [mmHg], the peak corresponding to DBP is recorded as 82 [mmHg], and the pulse rate PR is recorded as 61 [pulses/minute]. Although not illustrated for the sake of simplicity, for the blood pressure surge No. 2, the time-series data on the pulse-corresponding peaks of the individual waveform is recorded in the same manner.

Next, as shown in step S112 in FIG. 10, the control part 310 offsets each of the N individual waveforms, with making the start point P1 of each individual waveform as a base (=0 [mmHg]). That is, for each of the N individual waveforms, the blood pressure value (in this example, the SBP value) at the start point P1 is subtracted from the blood pressure value (in this example, the SBP value) at each time. As a result, the blood pressure variation amount data for each time is obtained. Such an offset allows the curve Cav indicating the mean waveform as the representative waveform and the waveform variation ±σ for each abscissa X to be easily grasped.

Next, as shown in step S113 in FIG. 10, the control part 310 specifies an individual waveform having the largest dimension in the X direction (horizontal direction) among the N individual waveforms. Further, the largest X-direction dimension is set as M pulses.

Next, as shown in step S114 in FIG. 10, the control part 310 allocates a memory area of N rows and M columns in the storage part 320 as a work area for computation.

Figure 13:
FIG. 13 is a diagram illustrating a table for use in statistical processing on blood pressure variation amount data.

For the sake of simplicity, as illustrated in FIG. 8, it is assumed that the number N of obtained blood pressure surges is equal to two, the X-direction dimension of the individual waveform C1 of the "surge No. 1" corresponds to 12 pulses, and the X-direction dimension of the individual waveform C2 of the "surge No. 2" corresponds to 17 pulses. At this time, the control part 310 specifies the individual waveform having the largest X-direction dimension as C2 and obtains the largest X-direction dimension as M pulses equal to 17 pulses. Then, as shown in the second and third rows of the table MT3 in FIG. 13, the control part 310 allocates a memory area of 2 rows and 17 columns in the storage part 320 as a work area for computation on the "surge No. 1" and the "surge No. 2". Note that, in practice, when the number N of obtained blood pressure surges is greater than two, a memory area of more than two rows is allocated. In the top row (first row) of the table MT3, the pulse numbers each indicating a corresponding X-direction coordinate are shown.

Next, as shown in step S115 in FIG. 10, the control part 310 relatively slides the N individual waveforms in the horizontal direction X in the memory area of N rows and M columns to align the positions (pulse numbers) of the peaks of the N individual waveforms. For example, in the example in FIG. 13, the positions of the peaks of the two individual waveforms C1, C2 of the "surge No. 1" and the "surge No. 2" are aligned with the position of the pulse number 10 (surrounded by a dashed circle) in the horizontal direction X. As a result, in the second row of the table MT3, the blood pressure variation amount data on the "surge No. 1" is represented as "0", "4", "10", "13", . . . , "11", "3" for the pulse numbers 4 to 15 (the unit is mmHg, and the same applies hereinafter). Further, in the third row of the table MT3, the blood pressure variation amount data on the "surge No. 2" is represented as "0", "2", "3", "5", . . . , "4", "2" for the pulse numbers 1 to 17. As described above, the state where the positions (pulse numbers) of the peaks of the N individual waveforms are aligned is equivalent to the state where the plurality of individual waveforms C1, C2 are relatively slid in the horizontal direction X on the coordinate plane Q illustrated in FIG. 8 to align the positions of the peaks of the plurality of individual waveforms C1, C2. This makes it easier to grasp the curve Cav indicating the mean waveform as the representative waveform and the waveform variation ±σ for each abscissa X. Note that the above-described offset (step S112 in FIG. 10) makes both the value at the start point (pulse number 4) of the individual waveform C1 of the "surge No. 1" and the value at the start point (pulse number 1) of the individual waveform C2 of the "surge No. 2" equal to "0".

Next, as shown in step S116 in FIG. 10, the control part 310 performs statistical processing (in this example, averaging) on the blood pressure variation amount data on the N individual waveforms for each pulse number (column) to obtain a mean value. For example, in the example in FIG. 13, the mean value of the blood pressure variation amount data on the individual waveforms of the "surge No. 1" and the "surge No. 2" is shown for each pulse number in the bottom row (fourth row) of the table MT3. The curve Cav indicating the mean waveform as the representative waveform is determined by the mean value for each pulse number.

At this time, for an individual waveform (in the above-described example, the "surge No. 1") that is shorter in X-direction dimension than the longest individual waveform (in the above-described example, the "surge No. 2") among the N individual waveforms, the control part 310 sets a contribution of a pulse equivalent portion shorter than the longest individual waveform to zero for the statistical processing on the blood pressure variation amount data. For example, in the example in FIG. 13, for portions where the individual waveform of the "surge No. 1" is shorter than the individual waveform of the "surge No. 2", that is, for a portion corresponding to the pulse numbers 1 to 3 and a portion corresponding to the pulse numbers 16 to 17, the contribution is set to zero for the statistical processing on the blood pressure variation amount data. As a result, even when the N individual waveforms are different in X-direction dimension from each other on the coordinate plane Q, the statistical processing on the blood pressure variation amount data can be performed without any difficulty.

Further, as shown in step S117 in FIG. 10, the control part 310 obtains the standard deviation a of the distribution of the blood pressure variation amount data on the N individual waveforms for each pulse number (column). A region of ±σ for each pulse number is defined as the region Sd indicating the waveform variation described above.

As described above, in this flow, the statistical processing only needs to be performed on the blood pressure variation amount data on the N individual waveforms for each pulse number (column). This allows a reduction in complexity of computation performed by the control part 310 as compared with a case where the statistical processing on the blood pressure variation amount data is continuously performed in the horizontal direction X.

Note that, in step S112 in FIG. 10 described above, in addition to the offset, for each of the N individual waveforms, of the start point P1 to the base (=0 [mmHg]), normalization may be performed so as to align the heights of the peaks of the N individual waveforms. This makes it easier to grasp the curve Cav indicating the mean waveform as the representative waveform and the waveform variation ±σ for each abscissa X.

(Display of Image Data in Hospital Terminal)

The hospital terminal 200A receives the image data Im as illustrated in FIG. 9B from the server 300 over the network 900.

Next, upon receipt of a display instruction from the user via the operation part 230 of the hospital terminal 200A, the control part 210 of the hospital terminal 200A acts as a part of the display processing part to display the image data Im on the display screen of the display device 240. At this time, the mean blood pressure variation amount (mean value of the difference L1 between the systolic blood pressure (SBP) value at the surge start point P1 and the systolic blood pressure (SBP) value at the peak point P2 illustrated in FIG. 7) and the value of the standard deviation c (or ±σ, ±2σ, ±3σ) of the distribution, and the like may be further displayed on the display screen of the display device 240.

The user can grasp the curve Cav indicating the representative waveform and the region Sd indicating the waveform variation among the blood pressure surges for the subject 90 by viewing the display screen of the display device 240. This is considered to be useful as information for use in evaluation of a cardiovascular disease risk or information for use in evaluation of a disease risk of a specific organ in addition to diagnosis and treatment of SAS.

Note that the user may input a transfer instruction via the operation part 230 of the hospital terminal 200A to transmit the image data Im to another hospital terminal 200B or the like other than the hospital terminal 200A.

[B. Applied Blood Pressure-Related Information Display Method]

Under the applied blood pressure-related information display method, image data is created and displayed as follows by using blood pressure time-series data in which the measurement time (time) and blood pressure output from the sphygmomanometer 400 are associated with each other and information indicating the physical condition specifying period output by the PSG device 500.

Figure 5B:
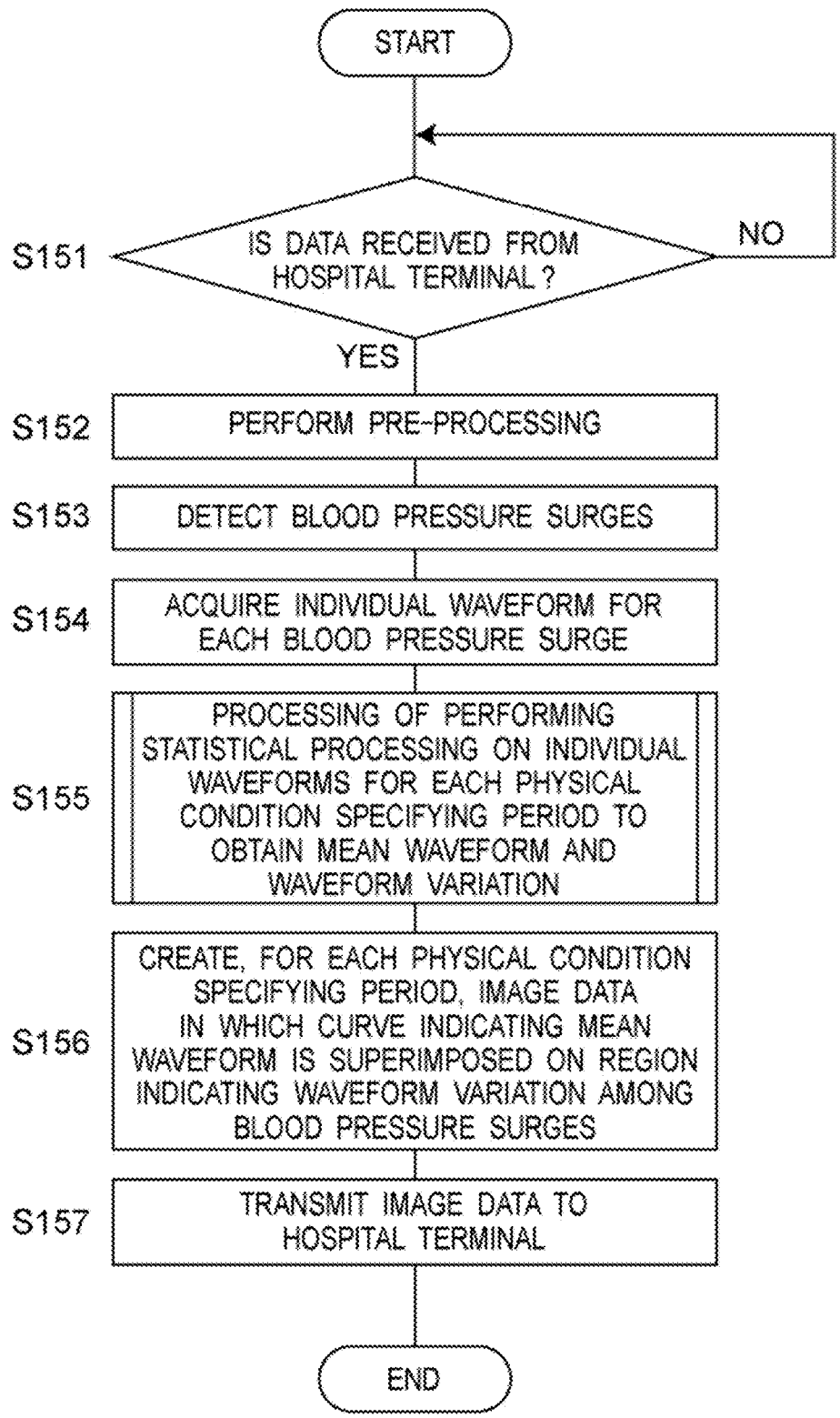
FIG. 5B is a diagram illustrating an operation flow of the server when executing an applied blood pressure-related information display method.

(Creation of Image Data in Server 300)

i) In the state illustrated in FIG. 4, it is assumed that continuous blood pressure measurement using the sphygmomanometer 400 and physical condition measurement using the PSG device 500 are performed on the subject 90 all night (including the sleep period). In this example, the blood pressure time-series data from the sphygmomanometer 400 and the information indicating the physical condition specifying period from the PSG device 500 are received by the hospital terminal 200A and temporarily stored in the memory 220. Subsequently, for example, a doctor as a user operates the operation part 230 of the hospital terminal 200A to transmit the blood pressure time-series data measured for the subject 90 together with the information indicating the physical condition specifying period to the server 300 over the network 900.

ii) In this example, the server 300 is in a continuous operation state (but a maintenance period or the like is excluded) and waits for data from the hospital terminal 200A as shown in step S151 in FIG. 5B (illustrating an operation flow of the server 300 when executing the applied blood pressure-related information display method). When the control part 310 of the server 300 receives the above-described data (the blood pressure time-series data and the information indicating the physical condition specifying period) from the hospital terminal 200A via the communication part 390 serving as an input part from the network 900 (YES in step S151), the received blood pressure time-series data and information indicating the physical condition specifying period are stored in the database 321 of the storage part 320. Then, the following steps S152 to S157 are executed.

iii) First, as shown in step S152, the control part 310 acts as the pre-processing part to perform pre-processing such as smoothing the blood pressure time-series data and removing noise from the blood pressure time-series data using a well-known moving average or the like, or removing high frequency components from the blood pressure time-series data using a low-pass filter.

iv) Next, as shown in step S153, the control part 310 acts as the blood pressure surge detection part to detect a blood pressure surge from the blood pressure time-series data on the subject 90 based on predetermined determination criteria as disclosed in, for example, Japanese patent application No. 2017-048946 and Japanese Patent Application No. 2017-050066. As a result, for example, a plurality of blood pressure surges are detected as indicated by dashed-line rectangular frames 803, 803, . . . in FIG. 6B. The "predetermined determination criteria" for detection of a blood pressure surge are the same as the determination criteria described for step S103 in FIG. 5A with reference to FIG. 7.

v) Next, as shown in step S154 in FIG. 5B, the control part 310 acts as the individual waveform acquisition part to acquire, for each of the detected blood pressure surges 803, 803 . . . , an envelope connecting a plurality of pulse-corresponding peaks (in this example, peaks corresponding to systolic blood pressure (SBP)) forming the blood pressure surge 803 as an individual waveform. As illustrated in FIG. 7, the individual waveform of the blood pressure surge is represented as a curve C having a mountain shape.

vi) Next, as shown in step S155 in FIG. 5B, the control part 310 acts as the statistical processing part to perform statistical processing on the plurality of individual waveforms acquired for each physical condition specifying period described above to obtain a representative waveform and waveform variation among the blood pressure surges in the time-series data 801 in this example. In this example, when a certain physical condition specifying period (for example, an apnea period) overlaps with the period from the start point P1 to the end point P4 of the blood pressure surge, the blood pressure surge is treated as having occurred in the physical condition specifying period. The "statistical processing" refers to processing of averaging the individual waveforms as described for step S105 in FIG. 5A with reference to FIG. 8 (and FIGS. 10 to 13). That is, the processing of averaging the individual waveforms of the blood pressure surges corresponds to processing of obtaining the curve Cav indicating the mean waveform as the representative waveform by averaging the blood pressure variation amount data on the plurality of individual waveforms C1, C2 for each abscissa X with the plurality of individual waveforms C1, C2 relatively slid in the horizontal direction X on the coordinate plane Q including the abscissae X representing the lapse of time and the ordinates Y representing the blood pressure variation amounts due to the blood pressure surges to align the positions of the peaks of the plurality of individual waveforms C1, C2. Further, in this example, a range of the "waveform variation" among the blood pressure surges is defined as a range of ±σ for each abscissa X using the standard deviation σ of distribution (distribution for each abscissa X) of the blood pressure variation amount data on the plurality of individual waveforms, as described for step S105 in FIG. 5A.

As a result, the curve Cav indicating the mean waveform as the representative waveform and the waveform variation ±σ for each abscissa X are obtained for each physical condition specifying period. For example, when the physical condition specifying period specified by the time-series data for one night includes four types of periods: an apnea period (including a hypopnea period), a REM sleep period, a non-REM sleep period, and an awakening period, the curve Cav indicating the mean waveform as the representative waveform and the waveform variation ±σ for each abscissa X are obtained for the apnea period. Likewise, for each of the REM sleep period, the non-REM sleep period, and the awakening period, the curve Cav indicating the mean waveform as the representative waveform and the waveform variation ±σ for each abscissa X are obtained.

vii) Next, as shown in step S156 in FIG. 5B, the control part 310 acts as a part of the display processing part to create, for each physical condition specifying period, image data Im where the curve Cav indicating the mean waveform is superimposed on the region Sd indicating the waveform variation among the blood pressure surges as illustrated in FIG. 9B.

Figure 15A:
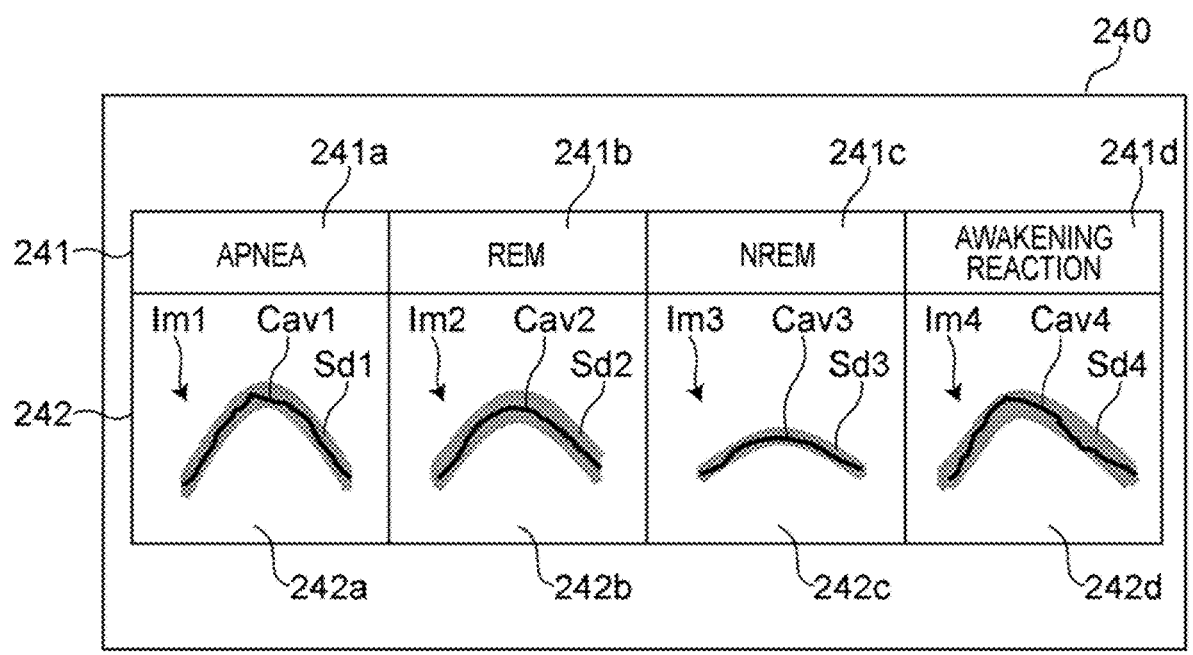
FIG. 15A is a diagram illustrating a state where pieces of image data where a curve indicating a mean waveform is superimposed on a region indicating a waveform variation, created separately for an apnea period, a REM sleep period, a non-REM sleep period, and an awakening period, are displayed side by side as thumbnails on a display screen.

For example, as illustrated in FIG. 15A to be described later, image data Im1, Im2, Im3, Im4 where curves Cav1, Cav2, Cav3, Cav4 each indicating the mean waveform are superimposed on regions Sd1, Sd2, Sd3, Sd4 each indicating the waveform variation are obtained for the apnea period (including the hypopnea period), the REM sleep period (REM), the non-REM sleep period (NREM), and the awakening period, respectively.

viii) Subsequently, as shown in step S157 in FIG. 5B, the control part 310 of the server 300 transmits, over the network 900, the image data Im1, Im2, Im3, Im4 created for each physical condition specifying period to the hospital terminal 200A, which is a provider of the blood pressure time-series data in this example.

Note that the control part 310 of the server 300 may transmit the image data Im1, Im2, Im3, Im4 to another hospital terminal 200B or the like other than the hospital terminal 200A, for example, in accordance with an instruction issued by the user who operates the hospital terminal 200A.

(Display of Image Data in Hospital Terminal)

Figure 14:
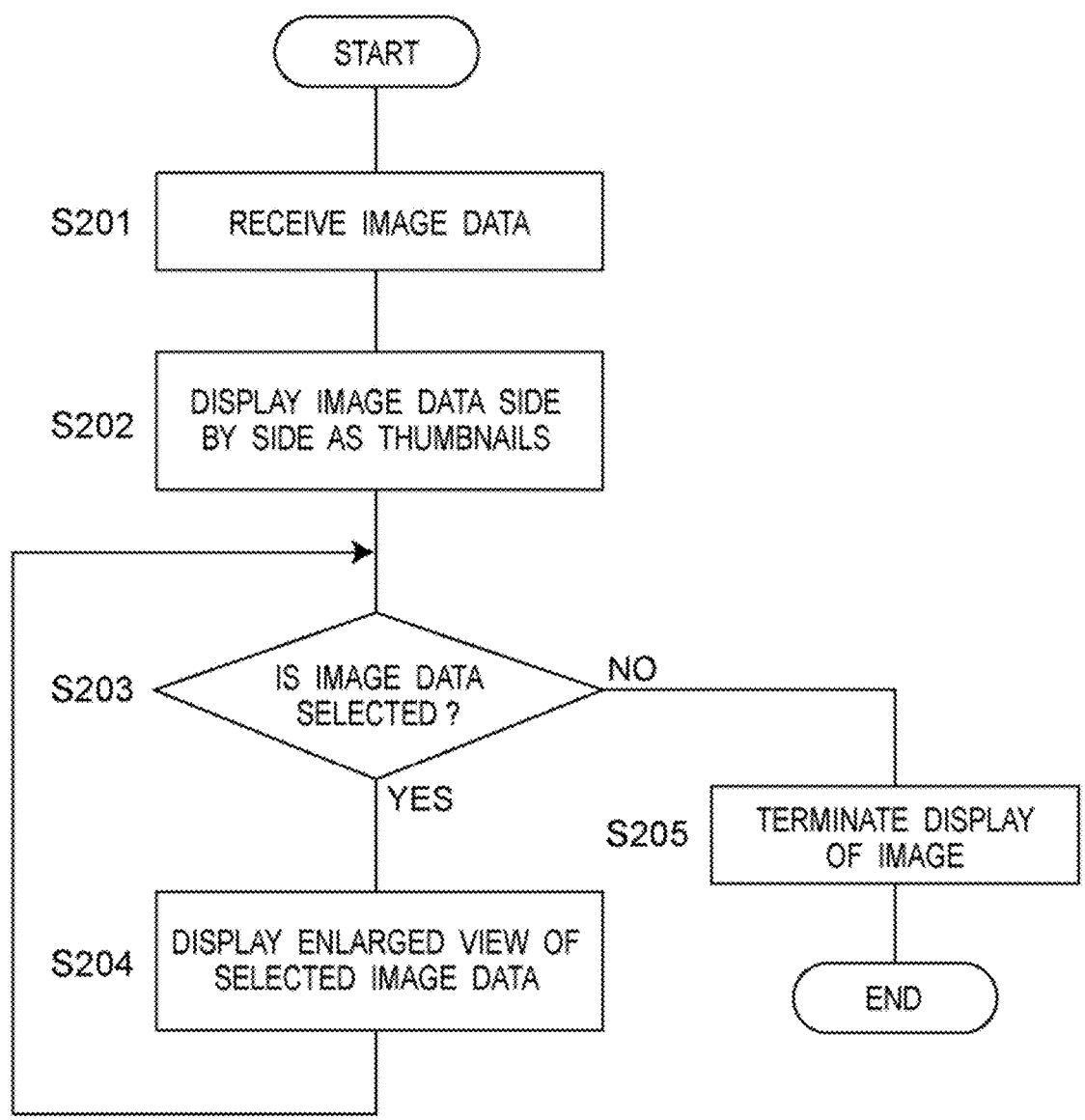
FIG. 14 is a diagram illustrating a flow of display processing in the hospital terminal when executing the applied blood pressure-related information display method.

FIG. 14 illustrates a flow of display processing performed by the hospital terminal 200A upon receipt of the image data created for each physical condition specifying period from the server 300. Note that, in this example, a description will be given with reference to the hospital terminal 200A, but another hospital terminal 200B and the like are also capable of performing the same display processing.

First, as shown in step S201 in FIG. 14, the hospital terminal 200A receives the image data created for each physical condition specifying period from the server 300 over the network 900. In this example, it is assumed that the physical condition specifying period includes four types of periods: the apnea period (including the hypopnea period), the REM sleep period, the non-REM sleep period, and the awakening period.

Next, the control part 210 of the hospital terminal 200A acts as a part of the display processing part to display, as illustrated in FIG. 15A, the image data Im1, Im2, Im3, Im4 created for each physical condition specifying period side by side as thumbnails on the display screen of the display device 240 (step S202 in FIG. 14). As illustrated in FIG. 15A, in this example, on the display screen of the display device 240, a physical condition specifying field 241 for specifying the physical condition specifying period and an image data field 242 disposed below the physical condition specifying field 241 are displayed on a one-to-one basis. In this example, the physical condition specifying field 241 includes, from left to right, an "apnea" field 241a indicating the apnea period, a" REM" field 241b indicating the REM sleep period, a "NREM" field 241c indicating the non-REM sleep period, and an "awakening reaction" field 241d indicating the awakening period. The image data field 242 includes a field 242a where the image data Im1 created for the apnea period is displayed, a field 242b where the image data Im2 created for the REM sleep period is displayed, a field 242c where the image data Im3 created for the non-REM sleep period is displayed, and a field 242d where the image data Im4 created for the awakening period is displayed.

In this example, the image data Im1 created for the apnea period corresponds to an image where the curve Cav1 indicating the mean waveform is superimposed on the region Sd1 indicating the waveform variation. The image data Im2 created for the REM sleep period corresponds to an image where the curve Cav2 indicating the mean waveform is superimposed on the region Sd2 indicating the waveform variation. The image data Im3 created for the non-REM sleep period corresponds to an image where the curve Cav3 indicating the mean waveform is superimposed on the region Sd3 indicating the waveform variation. Further, the image data Im4 created for the awakening period corresponds to an image where the curve Cav4 indicating the mean waveform is superimposed on the region Sd4 indicating the waveform variation.

The user can grasp, by viewing the thumbnail display of the image data Im1, Im2, Im3, Im4, the curve Cav indicating the representative waveform and the region Sd indicating the waveform variation among the blood pressure surges for the subject 90 for each physical condition specifying period, in other words, for each period in which the subject 90 is in a physical condition that may become a factor in blood pressure surge. This allows the user to easily grasp the factor (physical condition) in the most serious blood pressure surge, for example. For example, since the image data Im1 created for the apnea period among the image data Im1, Im2, Im3, Im4 shows the largest blood pressure variation amount, it may be determined that "apnea" causes the most serious blood pressure surge.

Figure 15B:
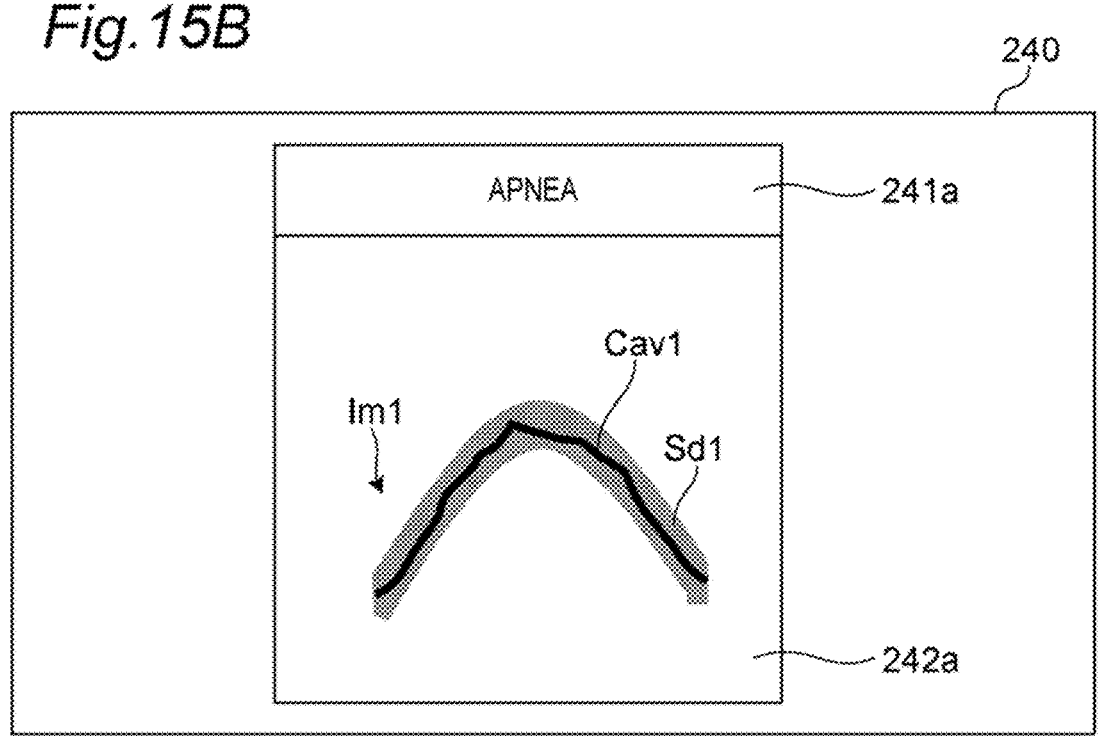
FIG. 15B is a diagram illustrating a state where the image data created for the apnea period is enlarged and displayed on the display screen.

Next, as shown in step S203 in FIG. 14, the control part 210 of the hospital terminal 200A determines whether or not the displayed image data Im1, Im2, Im3, Im4 is selected. When the user operates the operation part 230 to select any image data from among the image data Im1, Im2, Im3, Im4 (YES in step S203 in FIG. 14), the control part 210 displays an enlarged view of the image data (in this example, the image data Im1 created for the apnea period) for the selected physical condition specifying period on the display screen of the display device 240 as illustrated in FIG. 15B (step S204 in FIG. 14). At this time, the mean blood pressure variation amount (mean value of the difference L1 between the systolic blood pressure (SBP) value at the surge start point P1 and the systolic blood pressure (SBP) value at the peak point P2 illustrated in FIG. 7), the value of the standard deviation σ (or ±σ, ±2σ, ±3σ) of the distribution, and the like for the selected physical condition specifying period may be also displayed on the display screen of the display device 240.

When none of the image data Im1, Im2, Im3, Im4 is selected (NO in step S203 in FIG. 14), the control part 210 terminates the display of the image (step S205 in FIG. 14) to bring this display processing to an end.

Note that the user may input a transfer instruction via the operation part 230 of the hospital terminal 200A to transmit the image data Im1, Im2, Im3, Im4 to another hospital terminal 200B or the like other than the hospital terminal 200A.

As described above, displaying the image data Im1, Im2, Im3, Im4 where the curve indicating the mean waveform is superimposed on the region indicating the waveform variation among the blood pressure surges for each physical condition specifying period is considered to be useful as information for use in evaluation of a cardiovascular disease risk or information for use in evaluation of a disease risk of a specific organ in addition to diagnosis and treatment of SAS.

First Modification

According to the above-described embodiment, the server 300 creates the image data Im (or the image data Im1, Im2, Im3, Im4 for each physical condition specifying period, and the same applies hereinafter), and the display devices 240 of the hospital terminals 200A, 200B, . . . display the image, but the present invention is not limited to such a configuration. The control part 310 of the server 300 may transmit only data for use in image creation instead of transmitting the image data Im to the hospital terminals 200A, 200B, . . . and the control parts 210 of the hospital terminals 200A, 200B, . . . may exclusively create the image data Im.

Second Modification

Further, according to the above-described embodiment, the blood pressure-related information display device according to the present invention is configured as the system 100 on the network including the hospital terminals 200A, 200B, . . . and the server 300, but the blood pressure-related information display device is not limited to such a configuration.

For example, the blood pressure-related information display device according to the present invention may include only any one of the hospital terminals 200A, 200B, . . . . That is, the hospital terminal (for example, 200A) may execute all of the blood pressure-related information display method (including from receiving of the blood pressure time-series data from the sphygmomanometer 400 and the information indicating the physical condition specifying period from the PSG device 500 to displaying of the image data Im and the like on the display screen of the display device 240).

In such a case, a program for causing the control part 210 to execute the blood pressure-related information display method is installed in the memory 220 of the hospital terminal 200A. It is thus possible to make the blood pressure-related information display device according to the present invention small in size and compact.

Further, the above-described blood pressure-related information display method may be recorded as software (computer program) on a recording medium capable of storing data in a non-transitory manner such as a compact disc (CD), a digital versatile disc. (DVD), or a flash memory. Installing software recorded on such a recording medium into a practical computer device such as a personal computer, a personal digital assistant (PDA), or a smartphone allows the computer device to execute the above-described blood pressure-related information display method.

Third Modification

According to the above-described embodiment, the region Sd indicating the waveform variation constituting the image data Im is defined as a range of ±k times (typically ±α, ±2α, or ±3α) the standard deviation a of the distribution of the blood pressure variation amount data for each abscissa X. However, the range of the region Sd indicating the waveform variation is not limited to the range defined using the standard deviation a.

For example, the region Sd indicating the waveform variation may be defined as an interquartile range of the distribution of the blood pressure variation amount data for each abscissa X. That is, as processing, the pieces of blood pressure variation amount data are arranged in ascending order for each abscissa X. Then, the first quartile is defined as the lower limit of the region Sd, and the third quartile is defined as the upper limit of the region Sd. As a result, the region Sd indicating the waveform variation can be obtained.

As described above, the case where the region Sd indicating the waveform variation is defined as the interquartile range of the distribution of the blood pressure variation amount data for each abscissa X requires no high computational complexity as compared with the case where the region Sd is defined using the standard deviation a, which makes computation simple. It is therefore possible to contribute to an increase in processing speed and a reduction in memory usage.

Further, the "representative waveform" among the blood pressure surges refers to the mean waveform obtained as a result of averaging the plurality of individual waveforms, but is not limited to such a mean waveform. The "representative waveform" among the blood pressure surges may be the second quartile (median) of the distribution of the blood pressure variation amount data for each abscissa X. In this case, as processing, the representative waveform can be obtained as a result of arranging the pieces of blood pressure variation amount data in ascending order for each abscissa X and connecting the medians in the horizontal direction.

Fourth Modification

According to the above-described embodiment, the region Sd indicating the waveform variation constituting the image data Im is displayed as a region having the intermediate density between the density of the curve Cav indicating the representative waveform and the density of the background region Bg on the display screen of the display device 240, for example, as illustrated in FIG. 9B. However, the display of the region Sd indicating the waveform variation is not limited to the region having the intermediate density.

For example, FIG. 16A illustrates a plurality of individual waveforms C11, C12, C13, . . . , similar to FIG. 9A. In this case, as illustrated in FIG. 16B, curves Ci indicating the plurality of individual waveforms C11, C12, C13, . . . may be displayed with the curves Ci made distinguishable from a curve Cav' indicating the representative waveform so as to form a region Sd' indicating the waveform variation. In this example, the curve Cav' is displayed by a solid line, whereas the curves Ci indicating the plurality of individual waveforms C11, C12, C13, . . . are each displayed by a dashed line. In this example, image data where the curve Cav' indicating the representative waveform is superimposed on the region Sd' (including the plurality of curves Ci) indicating the waveform variation is denoted by Im'.

This allows the user to intuitively grasp the curve Cav' indicating the representative waveform and the region Sd' indicating the waveform variation among the blood pressure surges for the subject 90. The display of the curves Ci indicating the plurality of individual waveforms is useful for allowing the user to grasp a variation among the individual waveforms C11, C12, C13, . . . , for example, in a case where the number of individual waveforms is several or less.

Note that the curve Cav' indicating the representative waveform and the curves Ci indicating the plurality of individual waveforms C11, C12, C13, . . . only need to be distinguishable from each other. For example, the curve Cav' indicating the representative waveform may be displayed by a red solid line, whereas the curves Ci indicating the plurality of individual waveforms C11, C12, C13, . . . may be displayed by a blue solid line.

Further, when a threshold Nα (for example, Nα=10) is provided for the number N of blood pressure surges obtained for each physical condition specifying period, and the number N of blood pressure surges obtained is equal to or greater than the threshold Nα, the first image data Im including the region Sd (the region having a width of ±σ in the vertical direction and the intermediate density) indicating the waveform variation as illustrated in FIG. 9B may be created and displayed. On the other hand, when the number N of blood pressure surges obtained is less than the threshold value Nα, the second image data Im' including the region Sd' (the curves Ci indicating the plurality of individual waveforms C11, C12, C13, . . . ) indicating the waveform variation as illustrated in FIG. 16B may be created and displayed. The determination as to whether the number N of blood pressure surges is greater than the threshold Nα can be made by, for example, the control part 310 of the server 300 acting as a blood pressure surge number determination part.

Alternatively, for example, the control part 310 of the server 300 may create both the first image data Im including the region Sd indicating the waveform variation as illustrated in FIG. 9B and the second image data Im' including the region Sd' indicating the waveform variation as illustrated in FIG. 16B. In this case, for example, both the first image data and the second image data may be transmitted from the server 300 to the hospital terminal (for example, 200A), and the display of the first image data Im and the display of the second image data Im' may be switched on the display screen of the display device 240 in response to user input via the operation part 230 of the hospital terminal (for example, 200A).

Fifth Modification

Further, according to the above-described embodiment, the sphygmomanometer 400 is of a tonometry-type, but is not limited to such a type. The sphygmomanometer 400 may include a light emitting element that emits light toward an artery passing through a corresponding portion of the to-be-measured part and a light receiving element that receives reflected light (or transmitted light) of the light and continuously detect blood pressure based on a change in volume of a pulse wave of the artery (photoelectric type). Further, the sphygmomanometer 400 may include a piezoelectric sensor in contact with the to-be-measured part, detect distortion due to pressure in the artery passing through the corresponding portion of the to-be-measured part as a change in electric resistance, and continuously detect blood pressure based on the change in electric resistance (piezoelectric type). Furthermore, the sphygmomanometer 400 may include a transmission element that transmits a radio wave (transmission wave) toward the artery passing through the corresponding portion of the to-be-measured part and a reception element that receives a reflected wave of the radio wave, detect a change in distance between the artery and the sensor due to a pulse wave of the artery as a phase shift between the transmission wave and the reflected wave, and continuously detect blood pressure based on the phase shift (radio wave irradiation type). Further, as long as a physical quantity from which blood pressure can be obtained can be observed, different methods may be applied.

As described above, a blood pressure-related information display device according to the present disclosure is a blood pressure-related information display device that displays information on a blood pressure surge in a visualized form, the blood pressure surge corresponding to a phenomenon in which blood pressure rises over a plurality of pulses to reach a peak and then falls over a plurality of pulses, the blood pressure-related information display device comprising:
   a blood pressure surge detection part configured to detect, based on predetermined determination criteria, blood pressure surges from time-series data on blood pressure of a subject that varies with pulsation;
   an individual waveform acquisition part configured to acquire, for each blood pressure surge detected, an envelope connecting a plurality of pulse-corresponding peaks forming the blood pressure surge as an individual waveform;
   a statistical processing part configured to perform statistical processing on a plurality of individual waveforms acquired to obtain a representative waveform and waveform variation among the blood pressure surges in the time-series data; and
   a display processing part configured to display, on a display screen, a curve indicating the representative waveform with the curve superimposed on a region indicating the waveform variation among the blood pressure surges, wherein
   the statistical processing part creates, in a memory area, an equivalent state where the plurality of individual waveforms are relatively slid in a horizontal direction to align positions of peaks of the plurality of individual waveforms on a coordinate plane including abscissae representing a lapse of time and ordinates representing blood pressure variation amounts due to the blood pressure surges, and performs the statistical processing on blood pressure variation amount data on the plurality of individual waveforms for each of the abscissae to obtain the representative waveform and the waveform variation, and the statistical processing part sets, for an individual waveform that is shorter in horizontal dimension than a longest individual waveform among the plurality of individual waveforms, a contribution of a pulse equivalent portion shorter than the longest individual waveform to zero for the statistical processing on the blood pressure variation amount data.

As used herein, the "predetermined determination criteria" typically refer to criteria for detection of a blood pressure surge of a patient suffering from sleep apnea syndrome (SAS). For example, as disclosed in Japanese Patent Application No. 2017-048946 and Japanese Patent Application No. 2017-050066, the "predetermined determination criteria" refer to that a range from a surge start point to a surge peak point falls within a peak detection section (for example, a period of 15 pulses), that a difference (a blood pressure variation amount) between a systolic blood pressure value at the surge start point and a systolic blood pressure value at the peak point is equal to or greater than 20 mmHg (or 15 mmHg), that a period between the surge start point and the peak point is longer than a period of five pulses, and that a period between the peak point and a surge end point is longer than a period of seven pulses.

Further, the plurality of "pulse-corresponding peaks" forming the blood pressure surge used to create the envelope refers to peaks corresponding to systolic blood pressure in a continuous instantaneous blood pressure waveform. Note that the "pulse-corresponding peaks" may refer to peaks corresponding to a diastolic blood pressure (DBP) value.

Further, the "statistical processing" refers to processing of averaging the individual waveforms or processing of obtaining a median of the individual waveforms. The "representative waveform" among the blood pressure surges refers to, for example, a mean waveform obtained as a result of averaging the plurality of individual waveforms, a waveform corresponding to a median of the plurality of individual waveforms, or the like. The "waveform variation" among the blood pressure surges refers to, for example, a width of distribution of the plurality of individual waveforms.

Further, the "display screen" typically refers to a screen of a display device, but may be, for example, a paper surface output by a printer.

Further, for example, the "display" of the curve indicating the representative waveform on the display screen is typically provided in a mode where abscissae represent the lapse of time (for example, progress of pulses) and ordinates represent blood pressure variation amounts due to the blood pressure surges.

Herein, a "peak of the individual waveform" refers to a peak of each blood pressure surge and corresponds to a maximum pulse-corresponding peak among a plurality of pulse-corresponding peaks forming the blood pressure surge.

Further, the "equivalent state" means that data in the memory area only needs to be in a state equivalent to a state defined on the coordinate plane without the necessity of actually drawing and aligning the positions of the peaks of the plurality of individual waveforms on the coordinate plane.

In the blood pressure-related information display device according to the present disclosure, the blood pressure surge detection part detects, based on the predetermined determination criteria, blood pressure surges from the time-series data on blood pressure of a subject that varies with pulsation. The individual waveform acquisition part obtains, for each blood pressure surge thus detected, an envelope connecting a plurality of pulse-corresponding peaks forming the blood pressure surge as an individual waveform. The statistical processing part performs statistical processing on the plurality of individual waveforms thus acquired to obtain a representative waveform and waveform variation among the blood pressure surges in the time-series data. The display processing part displays, on a display screen, a curve indicating the representative waveform with the curve superimposed on a region indicating the waveform variation among the blood pressure surges. This allows a user (typically, medical personnel such as a doctor or a nurse, or may be a subject, and the same applies hereinafter) to intuitively grasp the curve indicating the representative waveform and the region indicating the waveform variation among the blood pressure surges for the subject by viewing the display screen. This is considered to be useful as information for use in evaluation of a cardiovascular disease risk or information for use in evaluation of a disease risk of a specific organ in addition to diagnosis and treatment of SAS.

In the blood pressure-related information display device, the statistical processing part creates, in a memory area, an equivalent state where the plurality of individual waveforms are relatively slid in a horizontal direction to align positions of peaks of the plurality of individual waveforms, and performs the statistical processing on blood pressure variation amount data on the plurality of individual waveforms, so that the representative waveform and the waveform variation can be easily grasped. Further, even when the plurality of individual waveforms are different in horizontal dimension from each other by the pulse equivalent portion equivalent to several pulses on the coordinate plane, it is possible to perform the statistical processing on the blood pressure variation amount data without any difficulty.

In the blood pressure-related information display device of one embodiment, each of the blood pressure variation amount data on the plurality of individual waveforms is a variation amount with a blood pressure value at a start point of the individual waveform made as a base.

The blood pressure-related information display device according to this embodiment allows the representative waveform and the waveform variation to be easily grasped.

In the blood pressure-related information display device of one embodiment, the blood pressure variation amount data on the plurality of individual waveforms is normalized to make the peaks of the plurality of individual waveforms equal in height to each other.

The blood pressure-related information display device according to this embodiment allows the representative waveform and the waveform variation to be grasped more easily.

In the blood pressure-related information display device of one embodiment, the abscissae representing a lapse of time are identified by pulse numbers specifying the pulse-corresponding peaks, and the statistical processing part performs the statistical processing on the blood pressure variation amount data on the plurality of individual waveforms for each of the pulse numbers.

Since the pulse interval is not constant due to the heartbeat, a period of one pulse at the time of occurrence of a blood pressure surge forming a certain individual waveform and a period of one pulse at the time of occurrence of a blood pressure surge forming another individual waveform may be different from each other. "The abscissae representing a lapse of time are identified by pulse numbers . . . " means that the elapse of time is represented by the progress of pulses regardless of the difference.

In the blood pressure-related information display device according to this embodiment, the abscissae representing the lapse of time are identified by pulse numbers specifying the pulse-corresponding peaks. It is therefore possible to easily grasp the representative waveform and the waveform variation regardless of a difference between a period of one pulse at the time of occurrence of a blood pressure surge forming a certain individual waveform and a period of one pulse at the time of occurrence of a blood pressure surge forming another individual waveform. Further, the statistical processing part only needs to perform, for each pulse number, the statistical processing on the blood pressure variation amount data on the plurality of individual waveforms. This allows a reduction in complexity of computation performed by the statistical processing part as compared with a case where the statistical processing on the blood pressure variation amount data is continuously performed in the horizontal direction.

In the blood pressure-related information display device of one embodiment,
  when k is a natural number, the waveform variation obtained by the statistical processing part is defined as ±k times a standard deviation of distribution of the blood pressure variation amount data on the plurality of individual waveforms, and
  the display processing part displays, on the display screen, a region having a width corresponding to ±k times the standard deviation in a vertical direction as the region indicating the waveform variation.

In the blood pressure-related information display device according to this embodiment, a region having a width corresponding to ±k times the standard deviation (where k is a natural number, and k is typically 1, 2, or 3) in the vertical direction as the region indicating the waveform variation is displayed on the display screen. This allows the user to intuitively grasp the curve indicating the representative waveform and the region indicating the waveform variation among the blood pressure surges for the subject. The display of the region indicating the waveform variation is particularly useful, for example, when the waveform variation among the individual waveforms is enough to be treated as a normal distribution (for example, when there are several tens or more individual waveforms).

In the blood pressure-related information display device of one embodiment,
  the waveform variation obtained by the statistical processing part is defined as an interquartile range of distribution of the blood pressure variation amount data on the plurality of individual waveforms, and
  the display processing part displays, on the display screen, a region having a width corresponding to the interquartile range in a vertical direction as the region indicating the waveform variation.

In the blood pressure-related information display device according to this embodiment, a region having a width corresponding to the interquartile range in a vertical direction is displayed on the display screen as the region indicating the waveform variation. This allows the user to intuitively grasp the curve indicating the representative waveform and the region indicating the waveform variation among the blood pressure surges for the subject. This eliminates the need for high computational complexity as compared with the case where the region indicating the waveform variation is defined using the standard deviation, which makes computation simple. It is therefore possible to contribute to an increase in processing speed and a reduction in memory usage.

In the blood pressure-related information display device of one embodiment, the display processing part displays, on the display screen, curves indicating the plurality of individual waveforms to form the region indicating the waveform variation with the curves made distinguishable from the curve indicating the representative waveform.

In the blood pressure-related information display device according to this embodiment, the curve indicating the representative waveform and the curves indicating the plurality of individual waveforms are displayed, on the display screen, to form the region indicating the waveform variation. This allows the user to intuitively grasp the curve indicating the representative waveform and the region indicating the waveform variation among the blood pressure surges for the subject. The display of the curves indicating the plurality of individual waveforms is useful for allowing the user to grasp a variation among the individual waveforms, for example, when the number of the individual waveform is several or less.

The blood pressure-related information display device of one embodiment further comprises an input part configured to input information indicating a physical condition specifying period in which a physical condition of the subject is specified, together with the time-series data on blood pressure of the subject that varies with pulsation, wherein
  the statistical processing part obtains the representative waveform and the waveform variation among the blood pressure surges in the time-series data for each physical condition specifying period, and
  the display processing part displays, on the display screen, the curve indicating the representative waveform with the curve superimposed on the region indicating the waveform variation among the blood pressure surges for each physical condition specifying period.

Herein, the "physical condition specifying period" refers to a period in which the subject is in a physical condition that may become a factor in blood pressure surge, such as an apnea period, a REM sleep period, a non-REM sleep period, an awakening period, and/or a period in which percutaneous arterial oxygen saturation ($SpO_2$) is low.

In the blood pressure-related information display device according to this embodiment, the input part inputs, together with the time-series data on blood pressure of the subject that varies with pulsation, information indicating the physical condition specifying period of the subject. The statistical processing part obtains the representative waveform and the waveform variation among the blood pressure surges in the time-series data for each physical condition specifying period. The display processing part displays, on the display screen, the curve indicating the representative waveform with the curve superimposed on the region indicating the waveform variation among the blood pressure surges for each physical condition specifying period. This allows the user to grasp the curve indicating the representative waveform and the region indicating the waveform variation among the blood pressure surges for the subject for each physical condition specifying period, in other words, for each period in which the subject is in a physical condition that may become a factor in blood pressure surge. This in turn allows the user to easily grasp a factor (physical condition) in the most serious blood pressure surge, for example.

In another aspect, a blood pressure-related information display method according to the present disclosure is a blood pressure-related information display method for displaying information on a blood pressure surge in a visualized form, the blood pressure surge corresponding to a phenomenon in which blood pressure rises over a plurality of pulses to reach a peak and then falls over a plurality of pulses, the blood pressure-related information display method comprising steps of:
  detecting, based on predetermined determination criteria, blood pressure surges from time-series data on blood pressure of a subject that varies with pulsation;
  acquiring, for each blood pressure surge detected, an envelope connecting a plurality of pulse-corresponding peaks forming the blood pressure surge as an individual waveform; and
  performing statistical processing on a plurality of individual waveforms acquired to obtain a representative waveform and waveform variation among the blood pressure surges in the time-series data, wherein
  on a coordinate plane including abscissae representing a lapse of time and ordinates representing blood pressure variation amounts due to the blood pressure surges, an equivalent state where the plurality of individual waveforms are relatively slid in a horizontal direction to align positions of peaks of the plurality of individual waveforms is created in a memory area, and the statistical processing is performed on blood pressure variation amount data on the plurality of individual waveforms for each of the abscissae to obtain the representative waveform and the waveform variation, and
  for an individual waveform that is shorter in horizontal dimension than a longest individual waveform among the plurality of individual waveforms, a contribution of a pulse equivalent portion shorter than the longest individual waveform is set to zero for the statistical processing on the blood pressure variation amount data; and further comprising
  displaying, on a display screen, a curve indicating the representative waveform with the curve superimposed on a region indicating the waveform variation among the blood pressure surges.

The blood pressure-related information display method according to the present disclosure allows the user to intuitively grasp the curve indicating the representative waveform and the region indicating the waveform variation among the blood pressure surges for the subject. This is considered to be useful as information for use in evaluation of a cardiovascular disease risk or information for use in evaluation of a disease risk of a specific organ in addition to diagnosis and treatment of SAS. Further, an equivalent state where the plurality of individual waveforms are relatively slid in a horizontal direction to align positions of peaks of the plurality of individual waveforms is created in a memory area, and the statistical processing is performed on blood pressure variation amount data on the plurality of individual waveforms, so that the representative waveform and the waveform variation can be easily grasped. Further, even when the plurality of individual waveforms are different in horizontal dimension from each other by the pulse equivalent portion equivalent to several pulses on the coordinate plane, it is possible to perform the statistical processing on the blood pressure variation amount data without any difficulty.

In yet another aspect, a computer-readable recording medium storing a program according to the present disclosure is a computer-readable recording medium non-transitorily storing a program for causing a computer to execute the above blood pressure-related information display method.

By making a computer read the program stored in the computer-readable recording medium according to the present disclosure and causing a computer to execute the program, the blood pressure-related information display method can be implemented.

As is apparent from the above, according to the blood pressure-related information display device and the blood pressure-related information display method according to the present disclosure, the representative waveform and the waveform variation among the blood pressure surges can be displayed in a superimposed manner. Further, when the computer executes the program stored in the computer-readable recording medium according to the present disclosure, the blood pressure-related information display method can be implemented.

The above embodiments are illustrative, and are modifiable in a variety of ways without departing from the scope of this invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A blood pressure-related information display device that displays information on a blood pressure surge in a visualized form, the blood pressure surge corresponding to a phenomenon in which blood pressure rises over a plurality of pulses to reach a peak and then falls over a plurality of pulses, the blood pressure-related information display device comprising:
  a processor programmed to act as
    a blood pressure surge detection part to detect, based on predetermined determination criteria, blood pressure surges from time-series data on blood pressure of a subject that varies with pulsation;
    an individual waveform acquisition part to acquire, for each blood pressure surge detected, an envelope connecting a plurality of pulse-corresponding peaks forming the blood pressure surge as an individual waveform;
    a statistical processing part to perform statistical processing on a plurality of individual waveforms acquired to obtain a representative waveform and waveform variation among the blood pressure surges in the time-series data;
    a display processing part to display, on a display screen, a curve indicating the representative waveform with the curve superimposed on a region indicating the waveform variation among the blood pressure surges;
  wherein the statistical processing part
    creates, in a memory area, an equivalent state where the plurality of individual waveforms are relatively slid in a horizontal direction to align positions of peaks of the plurality of individual waveforms on a coordinate plane including abscissae representing a lapse of time that are identified by pulse numbers specifying the pulse-corresponding peaks and ordinates representing blood pressure variation amounts due to the blood pressure surges, and performs the statistical processing on blood pressure variation amount data on the plurality of individual waveforms for each of the pulse numbers identifying the abscissae to obtain the representative waveform and the waveform variation; and sets, for an individual waveform that is shorter in a horizontal dimension than a longest individual waveform among the plurality of individual waveforms, a value or values of a pulse equivalent portion shorter than the longest individual waveform to zero for the statistical processing on the blood pressure variation amount data.

2. The blood pressure-related information display device according to claim 1, wherein each of the blood pressure variation amount data on the plurality of individual waveforms is a variation amount with a blood pressure value at a start point of the individual waveform made as a base.

3. The blood pressure-related information display device according to claim 1, wherein the blood pressure variation amount data on the plurality of individual waveforms is normalized to make the peaks of the plurality of individual waveforms equal in height to each other.

4. The blood pressure-related information display device according to claim 1, wherein when k is a natural number, the waveform variation is defined as ±k times a standard deviation of distribution of the blood pressure variation amount data on the plurality of individual waveforms, and the processor acting as the display processing part is configured to display, on the display screen, a region having a width corresponding to ±k times the standard deviation in a vertical direction as the region indicating the waveform variation.

5. The blood pressure-related information display device according to claim 1, wherein the waveform variation is defined as an interquartile range of distribution of the blood pressure variation amount data on the plurality of individual waveforms, and the processor acting as the display processing part is configured to display, on the display screen, a region having a width corresponding to the interquartile range in a vertical direction as the region indicating the waveform variation.

6. The blood pressure-related information display device according to claim 1, wherein the processor acting as the display processing part is configured to display, on the display screen, curves indicating the plurality of individual waveforms to form the region indicating the waveform variation with the curves made distinguishable from the curve indicating the representative waveform.

7. The blood pressure-related information display device according to claim 1, further comprising a network interface configured to input information indicating a physical condition specifying period in which a physical condition of the subject is specified, together with the time-series data on blood pressure of the subject that varies with pulsation, wherein the processor acting as the statistical processing part is configured to obtain the representative waveform and the waveform variation among the blood pressure surges in the time-series data for each physical condition specifying period, and the processor acting as the display processing part is configured to display, on the display screen, the curve indicating the representative waveform with the curve superimposed on the region indicating the waveform variation among the blood pressure surges for each physical condition specifying period.

8. A blood pressure-related information display method for displaying information on a blood pressure surge in a visualized form, the blood pressure surge corresponding to a phenomenon in which blood pressure rises over a plurality of pulses to reach a peak and then falls over a plurality of pulses, the blood pressure-related information display method comprising, by a programmed processor:

detecting, based on predetermined determination criteria, blood pressure surges from time-series data on blood pressure of a subject that varies with pulsation;

acquiring, for each blood pressure surge detected, an envelope connecting a plurality of pulse-corresponding peaks forming the blood pressure surge as an individual waveform; and performing statistical processing on a plurality of individual waveforms acquired to obtain a representative waveform and waveform variation among the blood pressure surges in the time-series data, wherein on a coordinate plane including abscissae representing a lapse of time that are identified by pulse numbers specifying the pulse-corresponding peaks and ordinates representing blood pressure variation amounts due to the blood pressure surges, an equivalent state where the plurality of individual waveforms are relatively slid in a horizontal direction to align positions of peaks of the plurality of individual waveforms is created in a memory area, and the statistical processing is performed on blood pressure variation amount data on the plurality of individual waveforms for each of the pulse numbers identifying the abscissae to obtain the representative waveform and the waveform variation, and for an individual waveform that is shorter in a horizontal dimension than a longest individual waveform among the plurality of individual waveforms, a value or values of a pulse equivalent portion shorter than the longest individual waveform is set to zero for the statistical processing on the blood pressure variation amount data; and the blood pressure-related information display method further comprising displaying, on a display screen, a curve indicating the representative waveform with the curve superimposed on a region indicating the waveform variation among the blood pressure surges.

9. A computer-readable recording medium non-transitorily storing a program for causing a computer to execute a blood pressure-related information display method according to claim 8.

* * * * *